US009089402B2

(12) United States Patent
Campbell et al.

(10) Patent No.: US 9,089,402 B2
(45) Date of Patent: Jul. 28, 2015

(54) ORTHOTIC JOINT AND KNEE-ANKLE-FOOT ORTHOTIC DEVICE INCORPORATING SAME

(75) Inventors: James H. Campbell, Clarkston, MI (US); Marie Christine Shamoun, Troy, MI (US); Michael Gallagher, Clinton Township, MI (US); Nicholas C. Zalinski, Macomb, MI (US)

(73) Assignee: Becker Orthopedic Appliance Company, Troy, MI (US)

( * ) Notice: Subject to any disclaimer, the term of this patent is extended or adjusted under 35 U.S.C. 154(b) by 656 days.

(21) Appl. No.: 13/464,980

(22) Filed: May 5, 2012

(65) Prior Publication Data

US 2013/0296754 A1 Nov. 7, 2013

(51) Int. Cl.
*A61F 5/37* (2006.01)
*A61B 19/00* (2006.01)
(Continued)

(52) U.S. Cl.
CPC ............... *A61F 5/0123* (2013.01); *A61F 5/00* (2013.01); *A61F 5/0102* (2013.01); *A61F 5/0125* (2013.01); *A61F 5/0127* (2013.01); *A61F 5/04* (2013.01); *A61F 5/05* (2013.01); *A61F 5/058* (2013.01); *A61F 5/0585* (2013.01); *A61F 5/05841* (2013.01); *A61F 5/37* (2013.01); *A61F 5/3761* (2013.01); *A61H 1/00* (2013.01); *A61H 1/02* (2013.01); *A61H 1/024* (2013.01); *A61H 1/0237* (2013.01); *A61H 1/0266* (2013.01); *A61F 2005/0158* (2013.01); *A61H 3/00* (2013.01)

(58) Field of Classification Search
CPC ........... A61F 5/00; A61F 5/01; A61F 5/0102;
A61F 5/0123; A61F 5/0127; A61F 5/0197;
A61F 5/04; A61F 5/05; A61F 5/058; A61F
5/05841; A61F 5/0585; A61F 5/37; A61F
5/3761; A61H 1/00; A61H 1/02; A61H
1/0237; A61H 1/024; A61H 1/0266; A61H
3/00
USPC ........ 128/846, 869, 878, 881, 882; 602/5, 12,
602/16, 20, 23, 26–27
See application file for complete search history.

(56) References Cited

U.S. PATENT DOCUMENTS 5,376,134 A 12/1994 Biedermann
6,979,304 B2 * 12/2005 Nijenbanning et al. ........ 602/16
(Continued)

OTHER PUBLICATIONS

Steven A. Gard, PHD, et al., The Influence of Four-Bar Linkage Knees on Prosthetic Swing-Phase Floor Clearance, Journal, 1996, pp. 34-40, vol. 8, Journal of Prosthetics and Orthotics, United States.
(Continued)

*Primary Examiner* — Alireza Nia
*Assistant Examiner* — Brandon L Jackson
(74) *Attorney, Agent, or Firm* — Antoinette M. Tease

(57) ABSTRACT

An orthotic joint comprising an upper plate, lower plate, cover plate, back plate, first link, second link, coil spring, and extension stop. The coil spring is situated between the lower plate and first link, and as the joint is flexed, the first end of the coil spring travels along a first arcuate edge of the first link. The extension is situated adjacent to the first link. A first pin pivotally connects the first link to the upper plate, a second pin pivotally connects the first link to the back plate, a third pin pivotally connects the second link to the upper plate, and a fourth pin pivotally connects the second link to the back plate. A knee-ankle-foot orthotic device comprising the orthotic joint of the present invention.

10 Claims, 25 Drawing Sheets

(51) Int. Cl.
*A61F 5/00* (2006.01)
*A61F 5/01* (2006.01)
*A61H 1/02* (2006.01)
*A61F 5/058* (2006.01)
*A61H 1/00* (2006.01)
*A61F 5/05* (2006.01)
*A61F 5/04* (2006.01)
*A61H 3/00* (2006.01)

(56) References Cited

U.S. PATENT DOCUMENTS 7,087,090 B2    8/2006    Andrysek et al.
2005/0149203 A1    7/2005    Andrysek et al.
2009/0143869 A1    6/2009    Cheng et al.

OTHER PUBLICATIONS

Dr. J. DeVries, MD, Conventional 4-bar Linkage Knee Mechanisms: A Strength-Weakness Analysis, Journal, Feb. 1995, pp. 36-42, vol. 32 No. 1, Journal of Rehabilitation Research and Development, United States.

C. W. Radcliffe, Four-Bar Linkage Prosthetic Knee Mechanisms: Kinematics, Alignment and Prescription Criteria, Journal, 1994, pp. 159-173, vol. 18, Prosthetics and Orthotics International, United States.

* cited by examiner

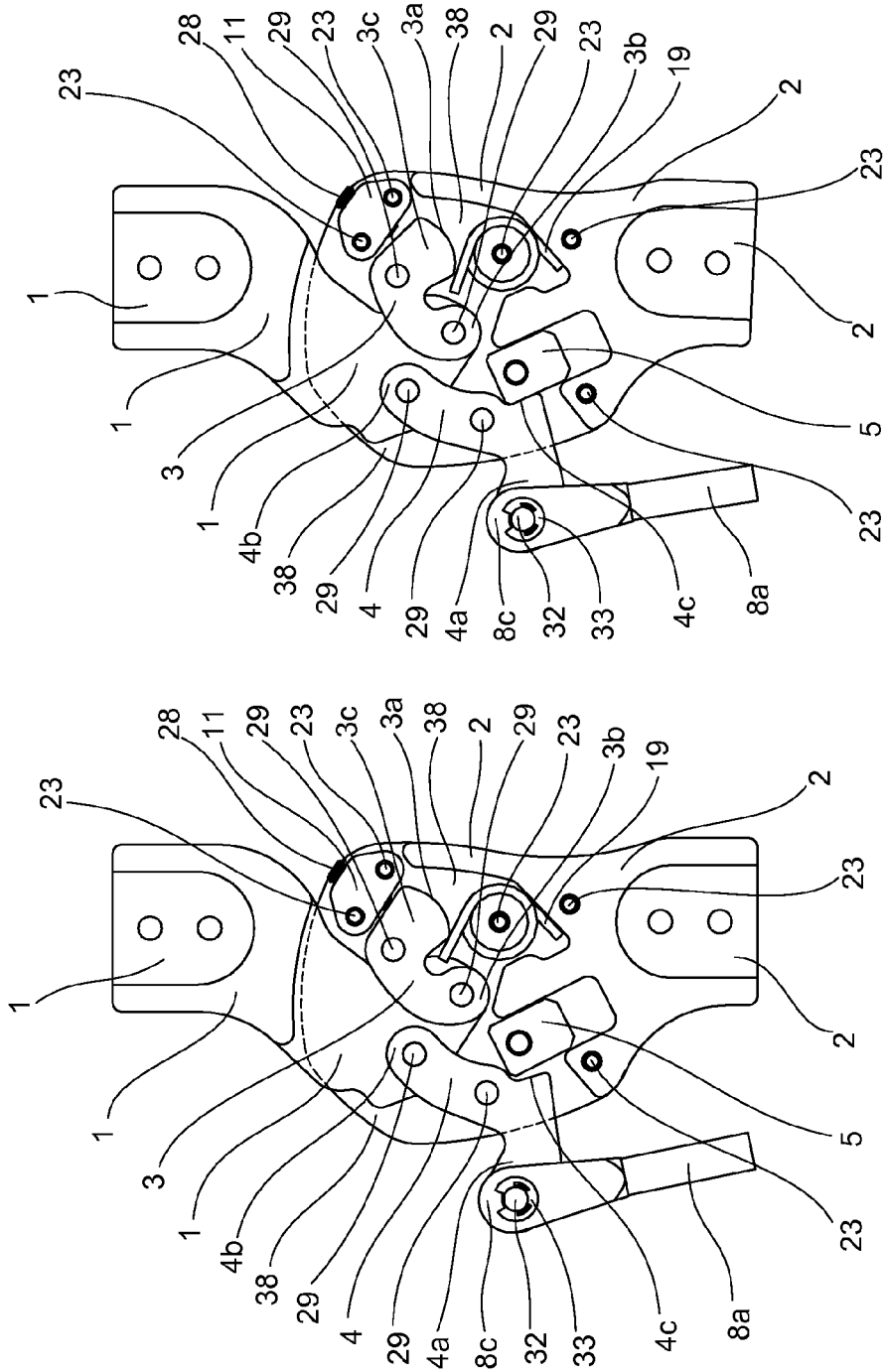

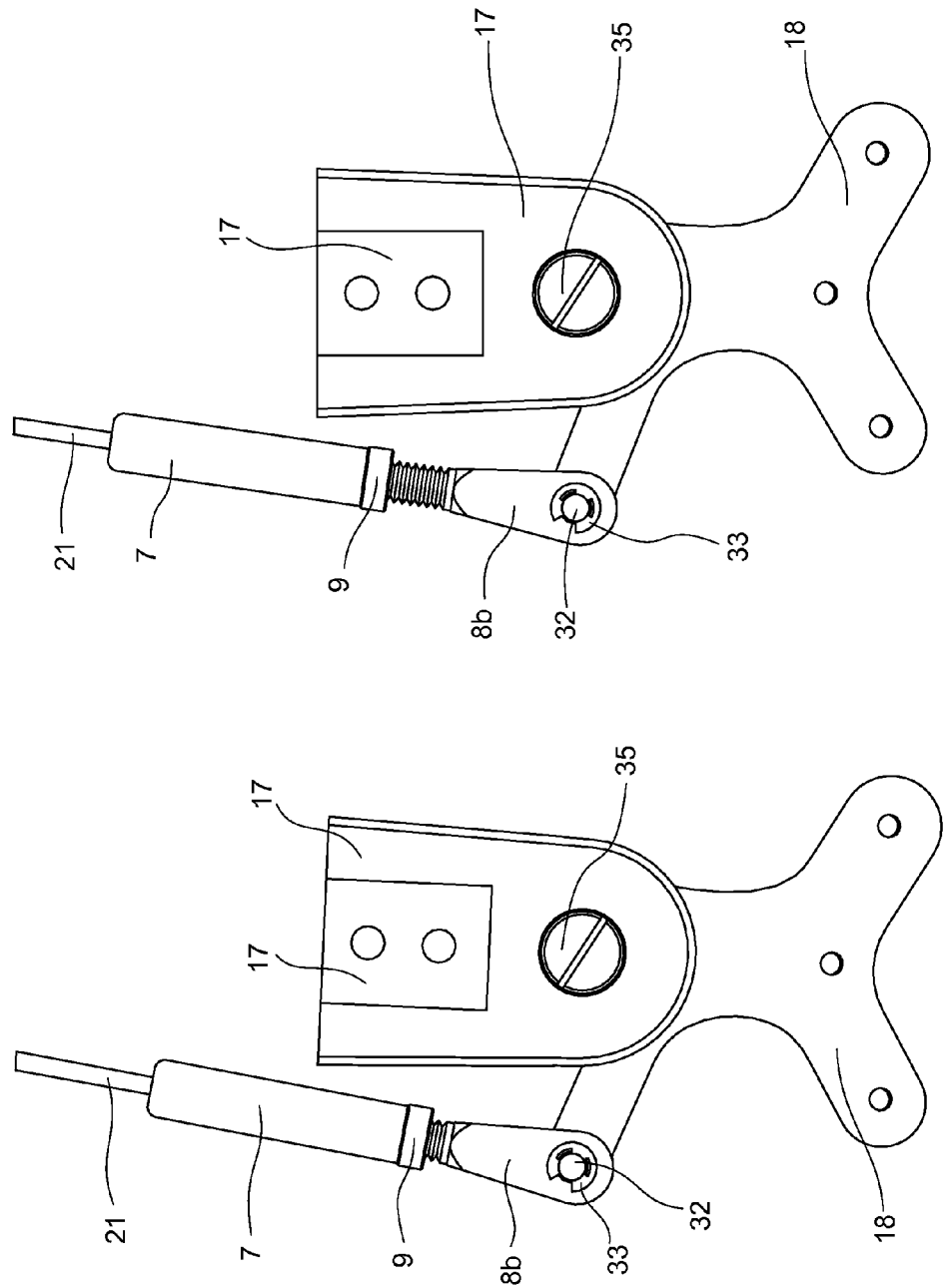

ORTHOTIC JOINT AND KNEE-ANKLE-FOOT ORTHOTIC DEVICE INCORPORATING SAME

BACKGROUND OF THE INVENTION

1. Field of the Invention

The present invention relates generally to the field of orthotics, and more particularly, to an orthotic joint with a link engagement mechanism and a knee-ankle-foot orthotic device that incorporates the orthotic joint.

2. Description of the Related Art

Orthotic devices are often provided for patients afflicted with polio, spinal cord injury, cerebrovascular accidents (e.g., stroke) and multiple sclerosis. In addition, patients suffering from nerve root injuries, other neurological or muscular diseases, or who experience secondary loss of control of the knee may require the use of an orthotic device. The problem that these orthotic devices attempt to address is the lack of knee control during the weight-bearing stages of the gait cycle.

Numerous attempts have been made to solve this problem, but none of the resulting products or inventions possesses the functionality and cost-effectiveness of the present invention. For example, the UTX® Swing Knee Ankle Foot Orthosis manufactured by Becker Orthopedic of Troy, Mich., is a device intended to stabilize the knee during the stance phase of gait but enable knee flexion during the swing phase. At the end of the swing phase, as the knee reaches full extension, a ratchet engages to stabilize the knee. At the end of the stance phase, as the ankle dorsiflexes, a cable linkage is used to unlock the knee joint and allow it to move freely.

The Free-Walk design manufactured by Otto Bock of Duderstadt, Germany and Minneapolis, Minn. creates a natural gait cycle by locking during the stance phase and unlocking during the swing phase. The automatic lock is initiated by knee extension and is only released to swing freely when a knee extension moment occurs simultaneously with ankle dorsiflexion in the terminal stance.

The Swing Phase Lock (SPL) manufactured by BASKO of Amsterdam, Netherlands automatically unlocks in order to allow knee flexion, and it locks before heel contact takes place. The SPL hinge system can only unlock when there is no flexion moment or strain of bending put on the hinge.

U.S. Pat. No. 4,632,096 (Harris, 1986) is an orthotic system for the leg that releases automatically upon a pre-selected dorsiflexion of the ankle followed by a pre-selected flexion of the ankle. The orthotic device is provided with a lock hinge that spans the pivoting means and locks the upper member and lower member when the leg approaches extension during a gait cycle.

U.S. Pat. No. 7,462,159 (Shlomovitz et al., 2008) is a knee-ankle-foot orthotic device with a low-profile cabling system that automatically unlocks at terminal stance to allow for free knee flexion and then reengage at mid-swing, permitting only knee extension (and not knee flexion). This feature ensures knee joint stability prior to heel contact and provides added safety, security and stability for individuals who fail to reach full knee extension.

Examples of other prior art knee braces and/or orthotic joints include U.S. Pat. No. 7,087,090 (Andrysek et al., 2006); U.S. Pat. No. 6,960,175 (Myers, 2005); U.S. Pat. No. 6,770,045 (Naft et al., 2004); U.S. Pat. No. 6,635,024 (Hatton et al., 2003); U.S. Pat. No. 6,517,503 (Naft et al., 2003); U.S. Pat. No. 6,159,248 (Grammas, 2000); U.S. Pat. No. 5,899,869 (Barrack, Jr., et al., 1999); U.S. Pat. No. 5,776,086 (Pansiera, 1998); U.S. Pat. No. 5,376,134 (Beidermann, 1994); U.S. Pat. No. 4,451,939 (Thompson, 1984); U.S. Pat. No. 2,943,622 (Nelson, 1960); U.S. Patent Application Pub. No. 2009/0143869 (Cheng et al.); U.S. Patent Application Pub. No. 20060211966 (Hatton et al.); U.S. Patent Application Pub. No. 2004/0049291 (Deharde et al.); U.S. Patent Application Pub. No. 2002/0183673 (Naft et al.); and U.S. Patent Application No. 20020269402 (Hatton et al.).

In contrast to prior art devices, the present invention utilizes a unique linkage mechanism to provide stability to the knee joint. This linkage mechanism includes a number of features not found in the prior art, namely, an adjustable extension stop, a stabilization/locking assist spring, a manual lock, a shock absorption feature, and a means for adjusting the cable length to affect how quickly the knee joints unlocks. These and other structural features and functional advantages of the present invention are discussed more fully below.

BRIEF SUMMARY OF THE INVENTION

The present invention is an orthotic joint comprising: an upper plate; a lower plate; a cover plate; a back plate; a first link; a second link; a coil spring that is situated between the lower plate and first link, wherein the coil spring comprises a first end, and wherein as the joint is flexed, the first end of the coil spring travels along a first arcuate edge of the first link; and an extension stop that is situated adjacent to the first link; wherein a first pin pivotally connects the first link to the upper plate, and a second pin pivotally connects the first link to the back plate; and wherein a third pin pivotally connects the second link to the upper plate, and a fourth pin pivotally connects the second link to the back plate.

In a preferred embodiment, the first link comprises a recess into which the first end of the coil spring recedes when the joint moves from an unlocked to a locked position. Preferably, the invention further comprises a lock and a knob, wherein the knob is attached to the lock and allows the position of the lock relative to the second link to be adjusted, wherein the second link comprises an inner wall, and wherein when the lock is in a locked position, the inner wall of the second link is in contact with the lock. The lock is preferably situated within a channel in the lower plate.

In a preferred embodiment, the invention further comprises an extension stop screw that is threadably inserted through the extension stop, and the extension stop screw adjusts the position of the second end portion of the first link relative to the extension stop. Preferably, the upper plate is attached to an upper leg brace, the lower plate is attached to a lower leg brace, the upper leg brace is attached to a thigh support, and the lower leg brace is attached to a calf support.

In a preferred embodiment, the invention further comprises: a cable with a first end and a second end, wherein the cable is secured to the upper and lower leg braces, and wherein the first end of the cable is attached to a first cable clevis, and the second end of the cable is attached to a second cable clevis; wherein the second link comprises a first end portion and a second end portion, and wherein the first cable clevis is pivotally attached to the second link such that when the cable is pulled downward, the first end portion of the second link rotates downward, and the second end portion of the second link rotates outward; wherein when the second end portion of the second link rotates outward, the upper plate moves in an outward direction; wherein the first link comprises a first end portion and a second end portion, and when the upper plate moves in an outward direction, the first end portion of the first link rotates upward, and the second end portion of the first link rotates downward; wherein the second cable clevis is pivotally attached to a stirrup; and wherein the stirrup is attached to a foot support and an ankle bracket.

Preferably, when the joint goes from an unlocked and partially flexed position to a fully flexed position, the first end portion of the second link rotates upward, the second end portion of the second link rotates inward, the first end portion of the first link rotates upward, and the second end portion of the first link rotates inward.

In one embodiment, the second cable clevis is threadably connected to a cable adjustment barrel, the cable has a length, and the length of the cable is adjusted by tightening and loosening the cable adjustment barrel on the second cable clevis. In an alternate embodiment, the first cable clevis is threadably connected to a cable adjustment barrel, the cable has a length, and the length of the cable is adjusted by tightening and loosening the cable adjustment barrel on the first cable clevis. The invention preferably further comprises a strain relief spring that is located inside of the cable adjustment barrel.

In a preferred embodiment, the ankle bracket comprises a first internal channel and a second internal channel; within the first internal channel are an ankle spring, a ball bearing situated on a first end of the ankle spring, and a set screw situated on a second end of the ankle spring, wherein the set screw adjusts compression of the ankle spring; and within the second internal channel are a rod, a ball bearing situated adjacent to a first end of the rod, and a set screw situated on a second end of the rod, wherein the set screw adjusts the position of the first end of the rod relative to the ball bearing. Preferably, the first internal channel is located in a rear end of the ankle bracket, and the second internal channel is located in a front end of the ankle bracket.

In yet another preferred embodiment, the invention is an orthotic joint comprising: an upper plate; a lower plate; a cover plate; a back plate that is roughly parallel to the cover plate; a first link; a second link; and an extension stop that is situated adjacent to the first link; wherein the lower plate is fixedly attached to the back plate; wherein a first pin pivotally connects the first link to the upper plate, and a second pin pivotally connects the first link to the back plate; and wherein a third pin pivotally connects the second link to the upper plate, and a fourth pin pivotally connects the second link to the back plate.

BRIEF DESCRIPTION OF THE DRAWINGS

FIG. 17A is a detail view of the knee joint assembly in a manually locked position without weight on the toe.

FIG. 17B is a detail view of the knee joint assembly in a manually locked position with weight on the toe.

FIG. 18A is a detail view of the ankle assembly with the cable adjustment barrel tightened.

FIG. 18B is a detail view of the ankle assembly with the cable adjustment barrel loosened.

REFERENCE NUMBERS

Figure 1:
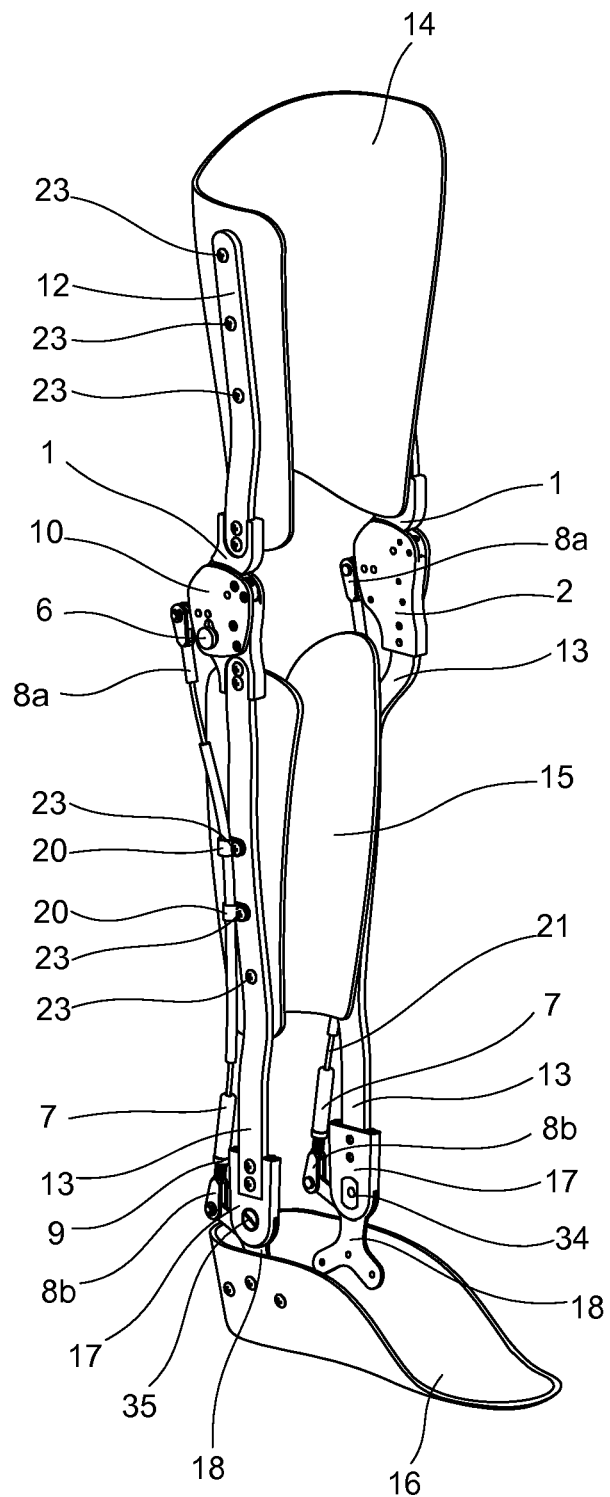
FIG. 1 is a perspective view of a knee-ankle-foot orthotic device incorporating the knee joint assembly of the present invention.

1 Upper plate
2 Lower plate
3 First link
3a First arcuate edge (of first link)
3b First end portion (of first link)
3c Second end portion (of first link)
4 Second link
4a First end portion (of second link)
4b Second end portion (of second link)
4c Inner wall (of second link)
5 Lock
6 Knob
7 Cable adjustment barrel
8a Cable clevis (non-threaded)

8b Cable clevis (threaded)
8c Twin brackets (of cable clevis)
9 Cable adjustment nut
10 Cover plate
10a Aperture (in cover plate)
11 Extension stop
12 Upper leg brace
13 Lower leg brace
14 Thigh support
15 Calf support
16 Foot support
17 Ankle bracket
18 Stirrup
19 Coil spring
20 Clip
21 Cable
22 Set screw
23 Screw
24 Ball bearing
25 Ankle spring
26 Rod
27 Strain relief spring
28 Extension stop screw
29 Pin
30 Upper leg assembly
31 Knee joint assembly
32 Cable pin
33 Retaining clip
34 T nut
35 Ankle screw
36 Lower leg assembly
37 Cable crimp
38 Back plate

DETAILED DESCRIPTION OF INVENTION

FIG. 1 is a perspective view of a knee-ankle-foot orthotic device incorporating the knee joint assembly of the present invention. As shown in this figure, the knee joint comprises an upper plate 1, a lower plate 2 and a cover plate 10. The upper plate 1 is attached to the upper leg brace 12, and the lower plate 2 is attached to the lower leg brace 13. The upper leg brace 12 in turn is attached to a thigh support 14 with screws 23, and the lower leg brace 12 is attached to a calf support 15 with screws 23. Extending from the cover plate 10 is a knob 6, the function of which is discussed below in connection with FIGS. 15-17.

A non-threaded cable clevis 8a is pivotally attached to the second link 4 (see FIG. 10) of the knee joint assembly. A threaded cable clevis 8b is pivotally attached to a stirrup 18, which in turn is attached to the foot support 16. As shown in FIG. 1, both stirrups 18 attached to a single foot support 16. Each stirrup 18 is also attached to an ankle bracket 17 with a T nut 34 and ankle screw 35, as shown.

The threaded cable clevis 8b is inserted into a cable adjustment barrel 7 and a cable adjustment nut 9. A cable 21 extends from the cable clevis 8a and terminates inside of the cable adjustment barrel 7. The purpose of the cable clevis 8b and cable adjustment barrel 7 is discussed below in connection with FIGS. 18-20. The cable 21 also passes through clips 20 that are attached to the lower leg brace 13.

Figure 2:
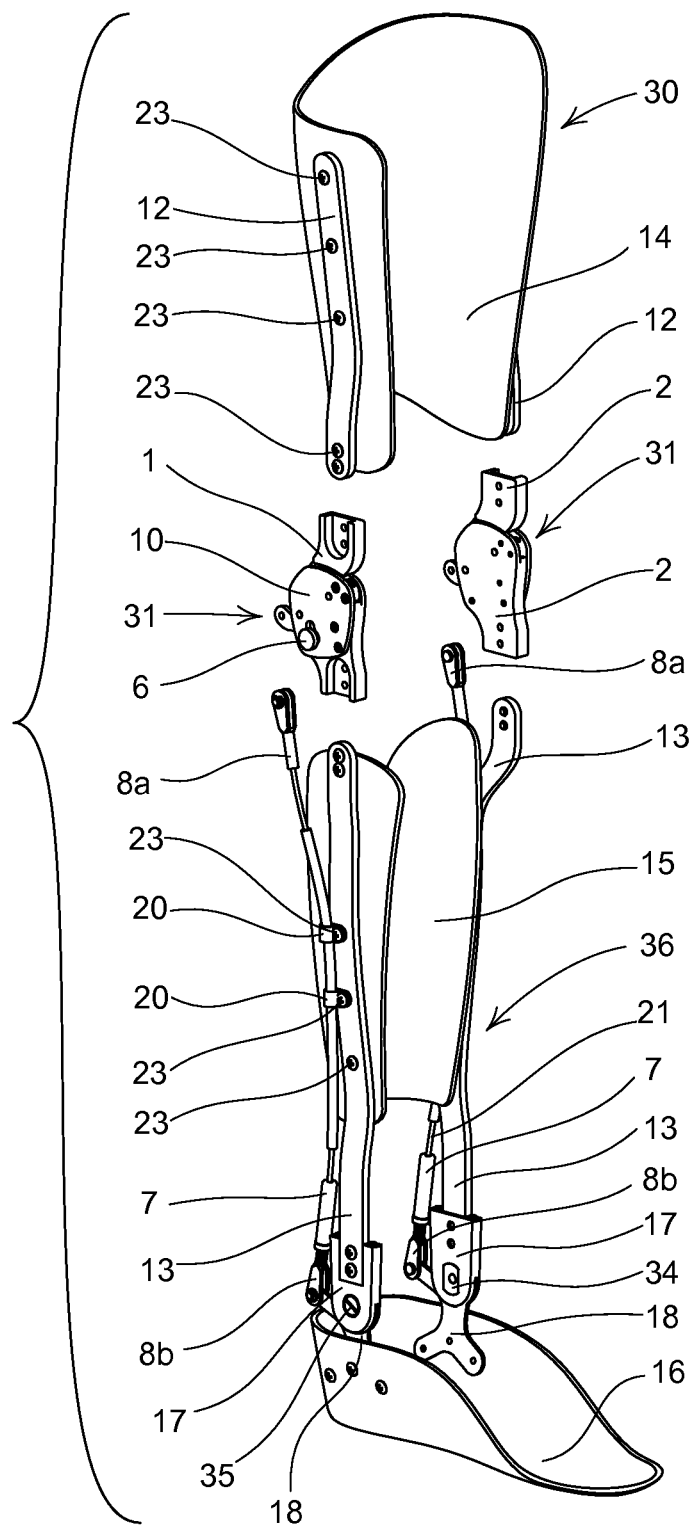
FIG. 2 is a partially exploded view of a knee-ankle-foot orthotic device incorporating the knee joint assembly of the present invention.

FIG. 2 is a partially exploded view of a knee-ankle-foot orthotic device incorporating the knee joint assembly of the present invention. As shown in this figure, the knee-ankle-foot-orthotic device comprises an upper leg assembly 30, a knee joint assembly 31, and a lower leg assembly 36. The upper leg assembly 30 is shown in an exploded view in FIG. 22. The lower leg assembly 36 is shown in an exploded view in FIG. 23. The knee joint assembly 31 is shown in an exploded view in FIG. 24.

Figure 3:
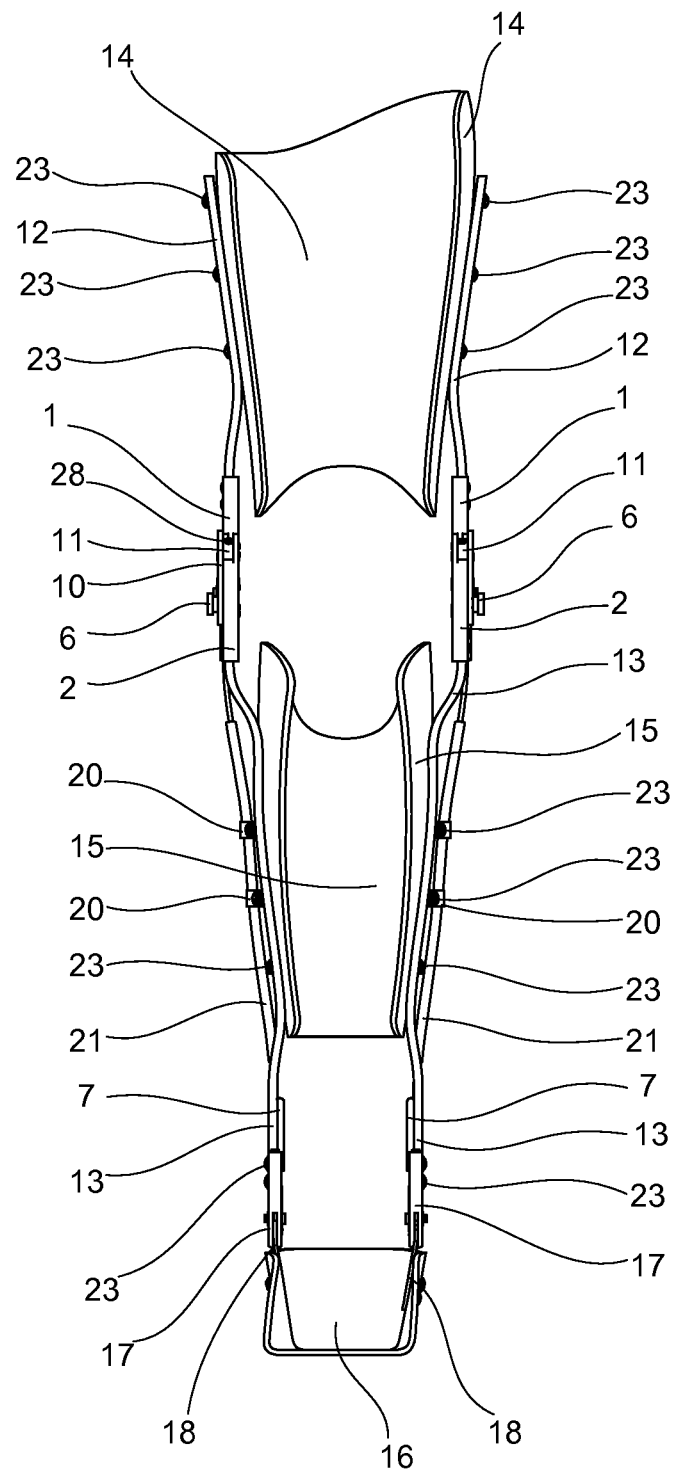
FIG. 3 is a front view of a knee-ankle-foot orthotic device incorporating the knee joint assembly of the present invention.

FIG. 3 is a front view of a knee-ankle-foot orthotic device incorporating the knee joint assembly of the present invention. As this figure illustrates, except for the shape of the thigh support 14, calf support 15 and foot support 16 (the calf support 15 and foot support 16 are drawn as symmetrical in the figures for ease of illustration, but the shape of these two parts would actually be non-symmetrically conformed to fit a patient's calf and foot, respectively), all other parts of the knee-ankle-foot orthotic device are identical (right and left) on either side of the supports 14, 15 and 16. Thus, the knee joint assembly 31 operates the same on either side of the knee. The upper leg braces 12 extend longitudinally along either side of the thigh support 14, the lower leg braces 13 extends longitudinally along either side of the calf support 15, and the two stirrups 18 are both attached to the foot support 16, as noted above.

FIGS. 4-9 collectively illustrate how the knee-ankle-foot orthotic device works during normal ambulation. These figures show the cable pin 32 and retaining clip 33, which are shown in greater detail in FIG. 25. Pins 29 serve to attach the cover plate 3 to various components of the linkage mechanism, which is shown more clearly in FIGS. 10-14.

Figure 4:
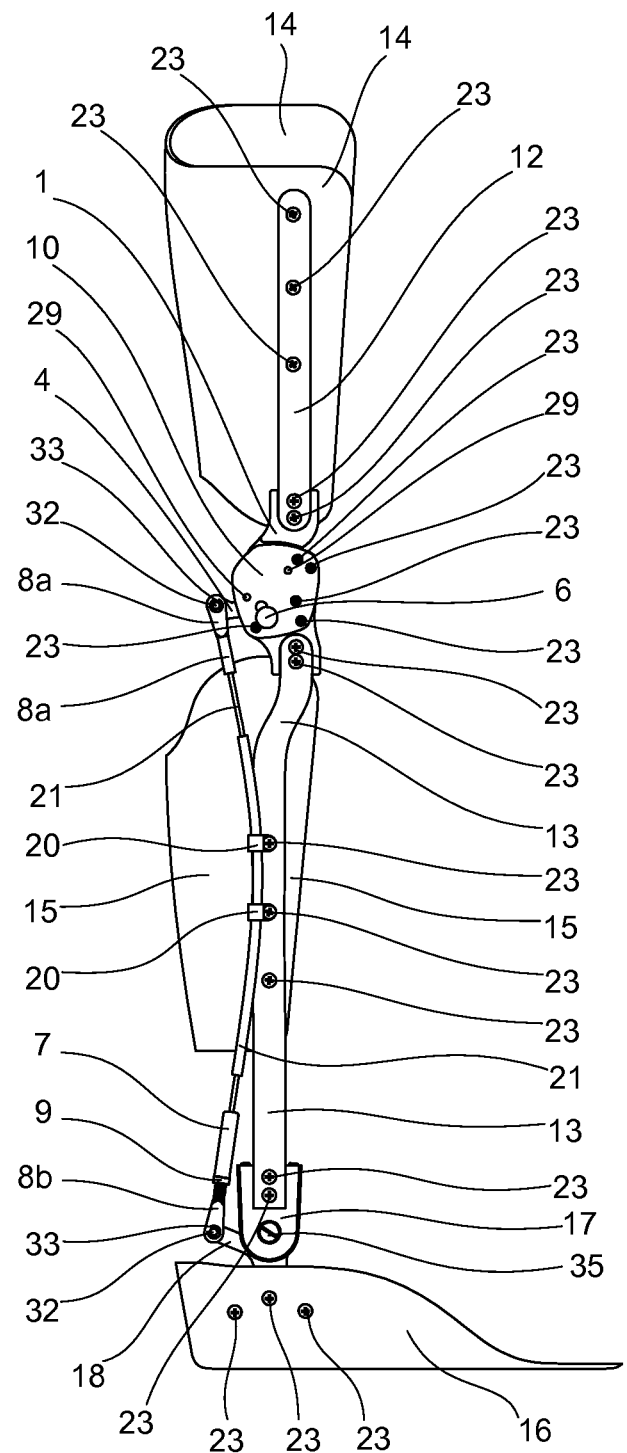
FIG. 4 is a right side view of a knee-ankle-foot orthotic device incorporating the knee joint assembly of the present invention shown in a vertical resting position with the knee joint locked.

In FIG. 4, both the knee and the ankle are unflexed, and the patient is standing still. (For ease of reference, the knee-ankle-orthotic device is shown without a patient wearing it in FIG. 4-9, but these figures illustrate what would happen if a patient were wearing the device.) Note that the knob 6 on both sides of the knee-ankle-foot device must be in an unlocked position in order for the knee to flex. In the first stage of the gait cycle, the ankle dorsiflexes (see FIG. 5). As this happens, the cable 21 is pulled downward (toward the foot support 16), and the first end portion 4a of the second link 4 that is attached to the cable clevis 8a rotates downward. This downward rotation of the first end portion 4a of the second link 4 causes the upper plate 1 and first link 3 to rotate, as shown in FIGS. 10-14. This rotation of the upper plate 1 and first link 3 allows the knee to flex (see FIGS. 6 and 7).

Figure 7:
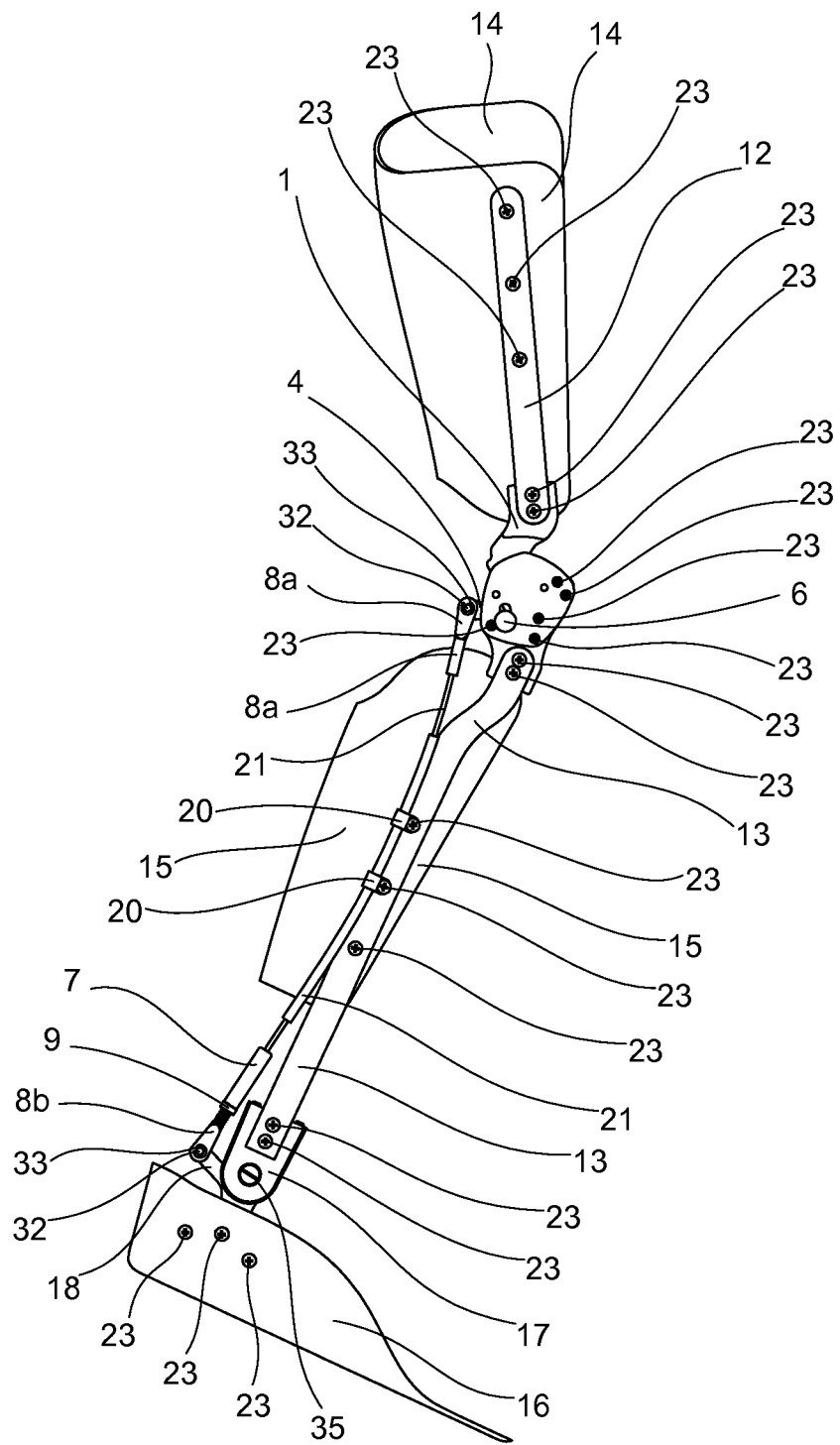
FIG. 7 is a right side view of a knee-ankle-foot orthotic device incorporating the knee joint assembly of the present invention shown in the swing phase of the gait cycle with the knee joint unlocked.
Figure 8:
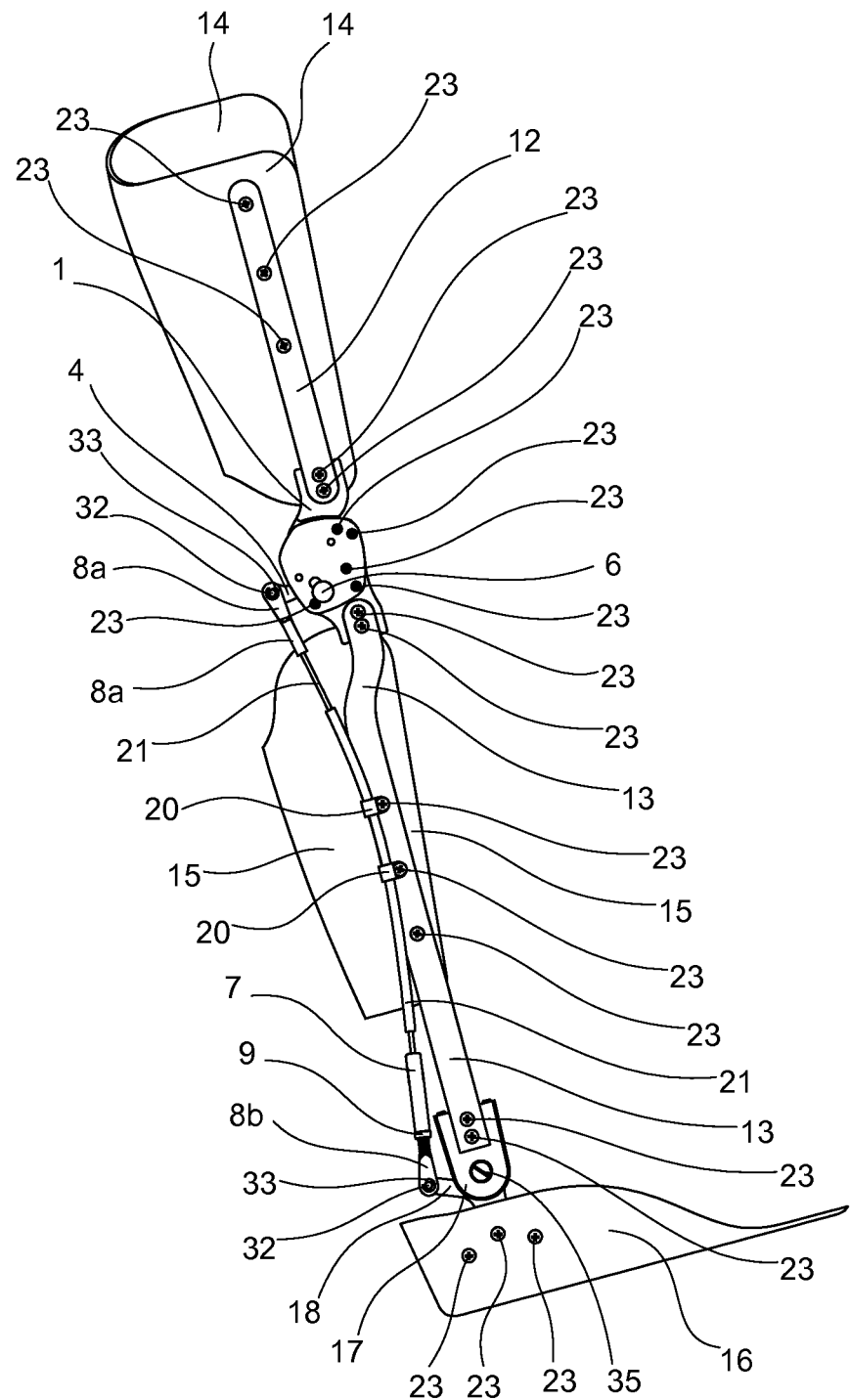
FIG. 8 is a right side view of a knee-ankle-foot orthotic device incorporating the knee joint assembly of the present invention shown with the knee joint locked before the heel touches the ground.
Figure 9:
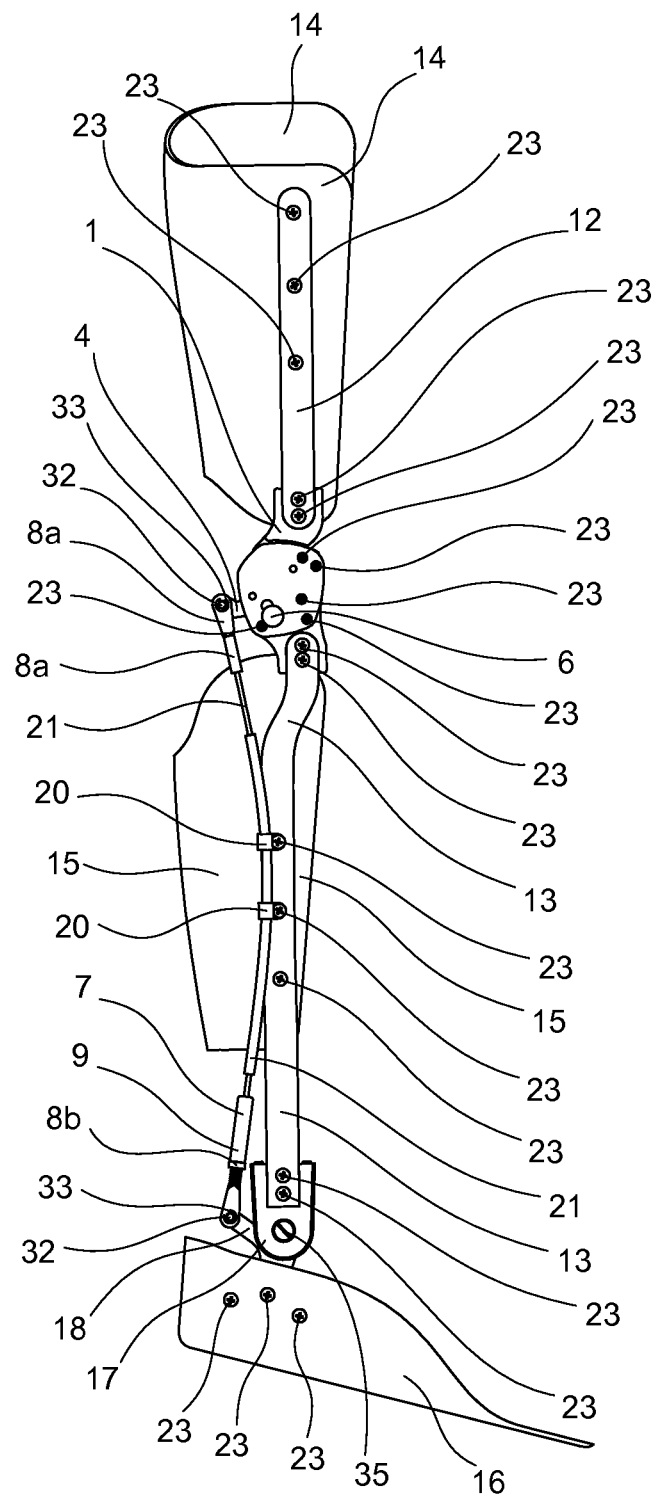
FIG. 9 is a right side view of a knee-ankle-foot orthotic device incorporating the knee joint assembly of the present invention shown with the knee joint locked after the heel touches the ground.

In FIG. 7, the leg is in the swing phase of the gait cycle. In FIG. 8, the leg straightens out just before the heel makes contact with the ground. In this position, the cable returns to its original position (the same one shown in FIG. 4), and the knee again cannot flex unless the ankle is dorsiflexed. In FIG. 9, the knee joint is locked, and the heel is on the ground, thereby completing the gait cycle.

Figure 10:
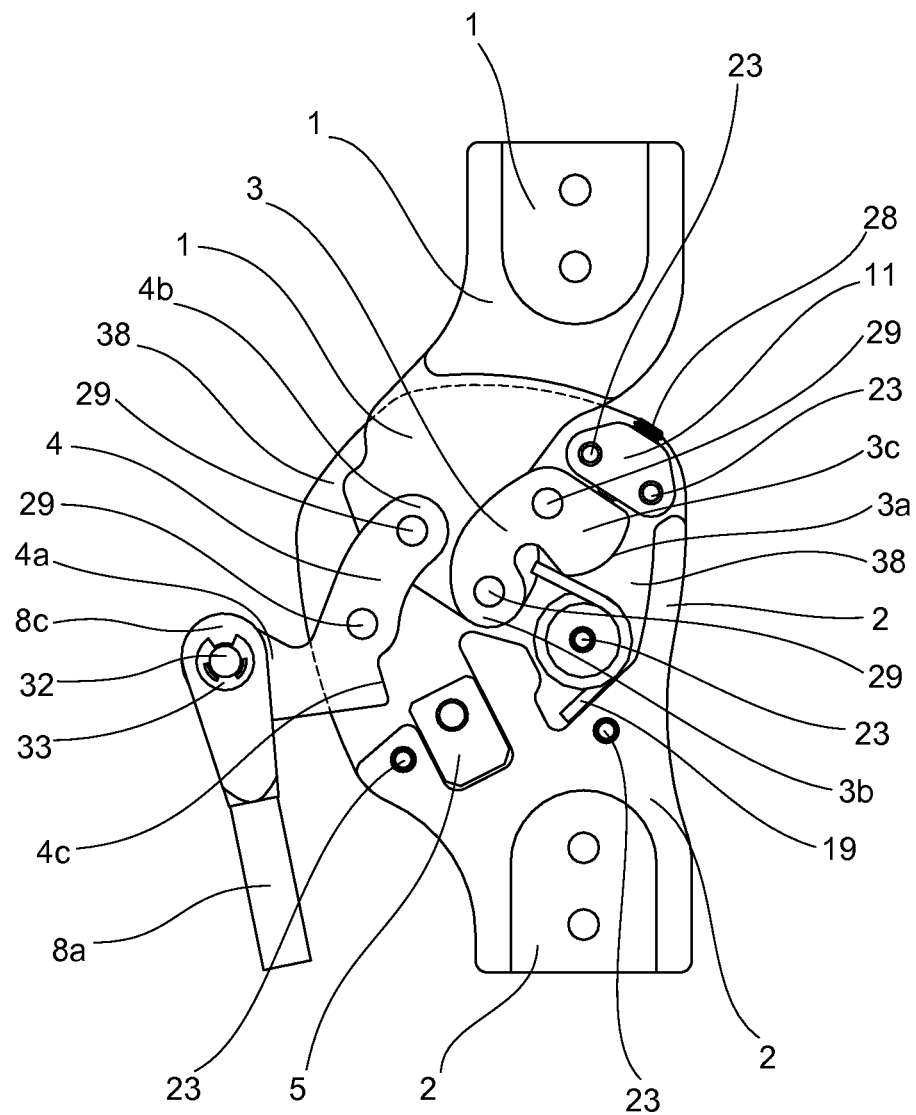
FIG. 10 is a detail view of the knee joint assembly of the present invention corresponding to the view shown in FIG. 4.

FIG. 10 is a detail view of the knee joint assembly of the present invention corresponding to the view shown in FIG. 4. As shown in this figure, the knee joint assembly 31 comprises a first link 3, a second link 4, an extension stop 11, a coil spring 19 and a lock 5. In this figure and in FIGS. 11-14, the knob 6 that is attached to the lock 5 has been removed for clarity (the knob 6 simply allows a user to move the lock between an unlocked and locked position). The extension stop screw 28 allows the degree of rotation of the first link 3 to be adjusted, as explained more fully below in connection with FIGS. 16A and 16B.

Screws 23 secure the lower plate 2 and extension stop 11 to the cover plate (not shown). One screw 23 also serves to hold the coil spring 19 in place (that is, it extends through the center of the coil spring 19) and is secured to the cover plate (not shown). Pins 29 serve as rotation points for the various components of the knee joint assembly. Two pins 29 extend through the first link 1 and allow it to rotate relative to the upper plate 1 and back plate 38. Two pins 29 extend through the second link 4 and allow it to rotate relative to the upper plate 1 and back plate 38. As noted above, the cable clevis 8a is pivotally attached to the second link 4.

The coil spring 19 is situated between the lower plate 2 and first link 3. The lower plate 2 comprises a recess into which a first end of the coil spring 19 is inserted, and the first link 3 comprises a recess into which a second end of the coil spring 19 is inserted. As the knee is flexed, the first end of the coil spring 19 travels along a first arcuate edge 3a of the first link 3. The coil spring 19 is most compressed when the knee joint is fully flexed (see FIG. 15). As the knee is extended again, the coil spring 19 travels back along the first arcuate edge 3a of the first link 3 until the first end of the coil spring 19 snaps back into place inside of the recess in the first link 3 as the spring slightly decompresses. This decompression of the spring acts as an assist for the knee joint to return to a locked (extended) position.

Figure 5:
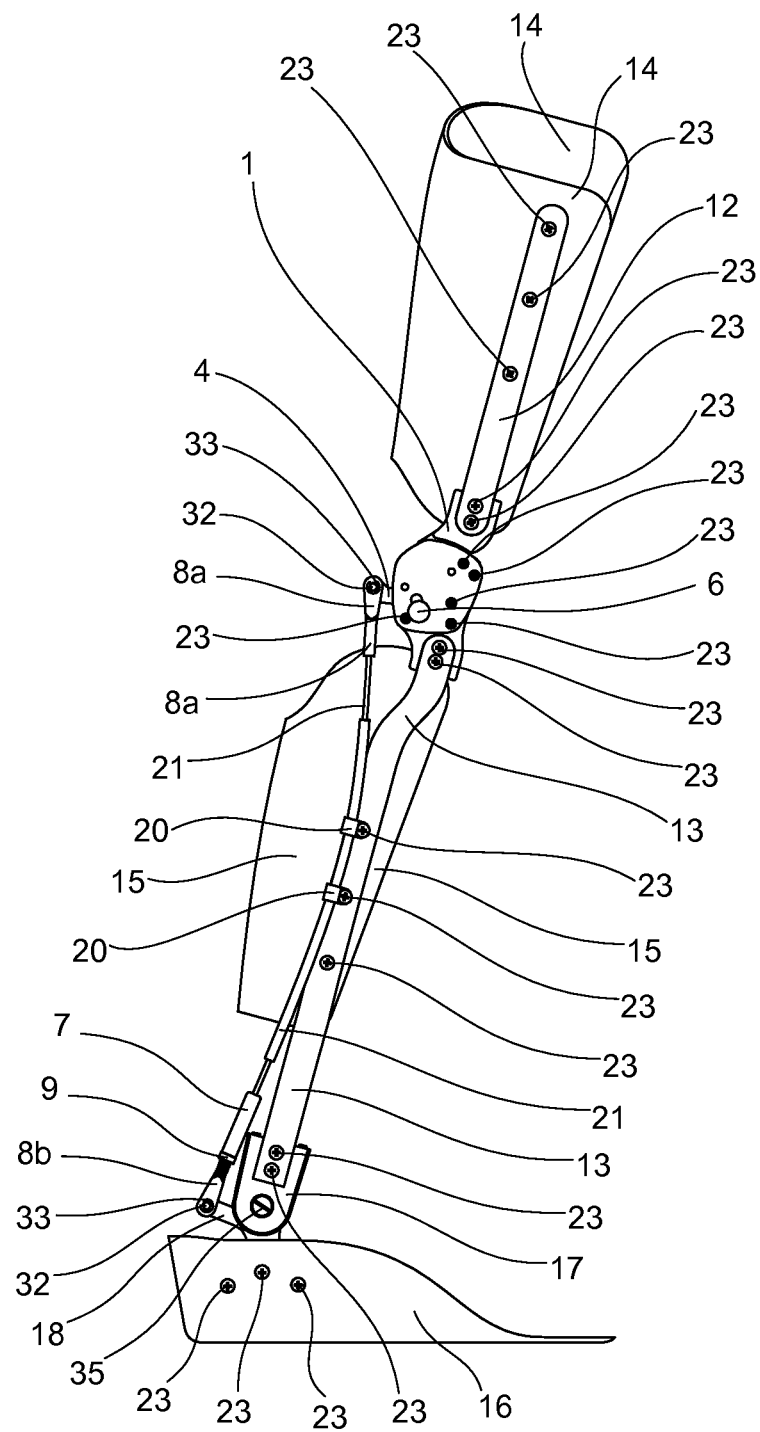
FIG. 5 is right side view or a knee-ankle-foot orthotic device incorporating the knee joint assembly of the present invention shown with the ankle dorsiflexed and the knee joint locked.
Figure 11:
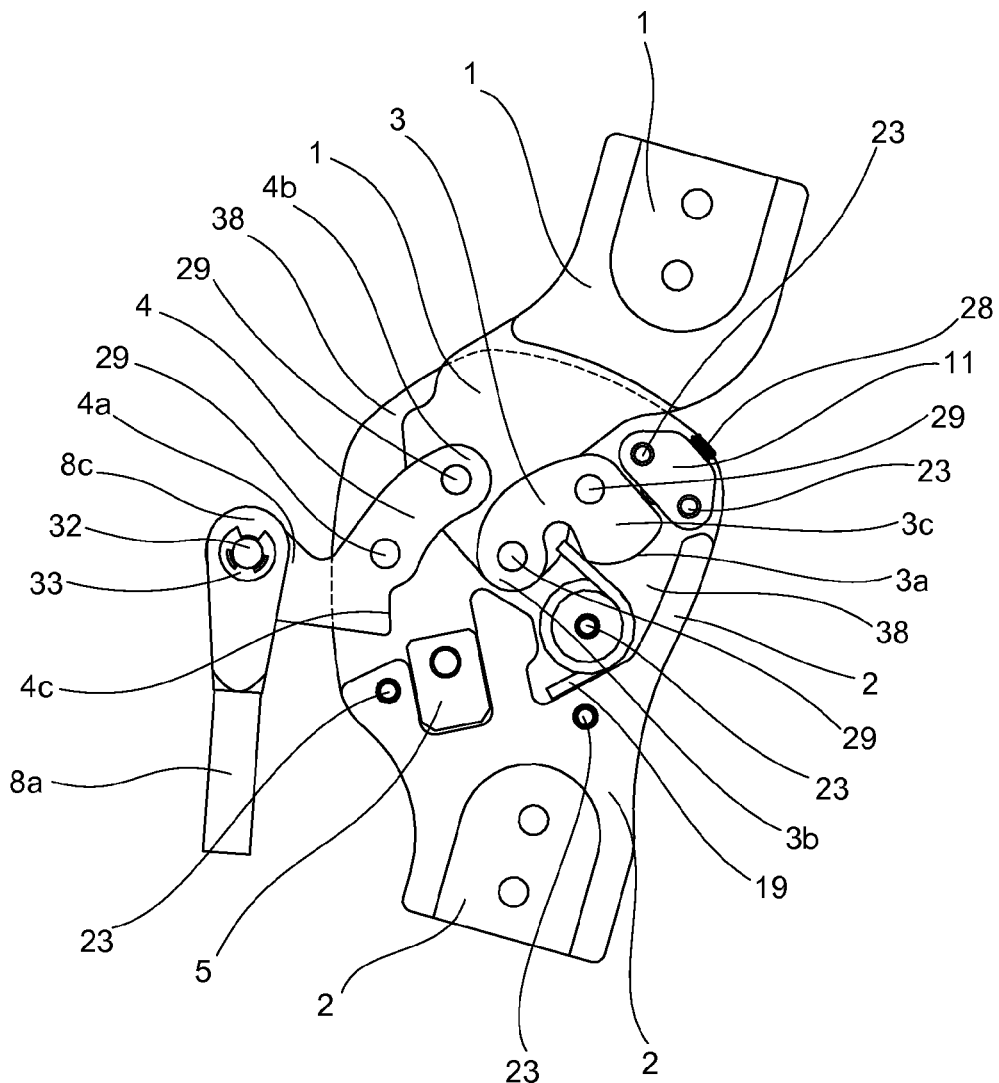
FIG. 11 is a detail view of the knee joint assembly of the present invention corresponding to the view shown in FIG. 5.

FIG. 11 is a detail view of the knee joint assembly of the present invention corresponding to the view shown in FIG. 5. This figure is identical to FIG. 10 except that the knee joint is at an angle because the ankle is dorsiflexed (see FIG. 5).

Figure 6:
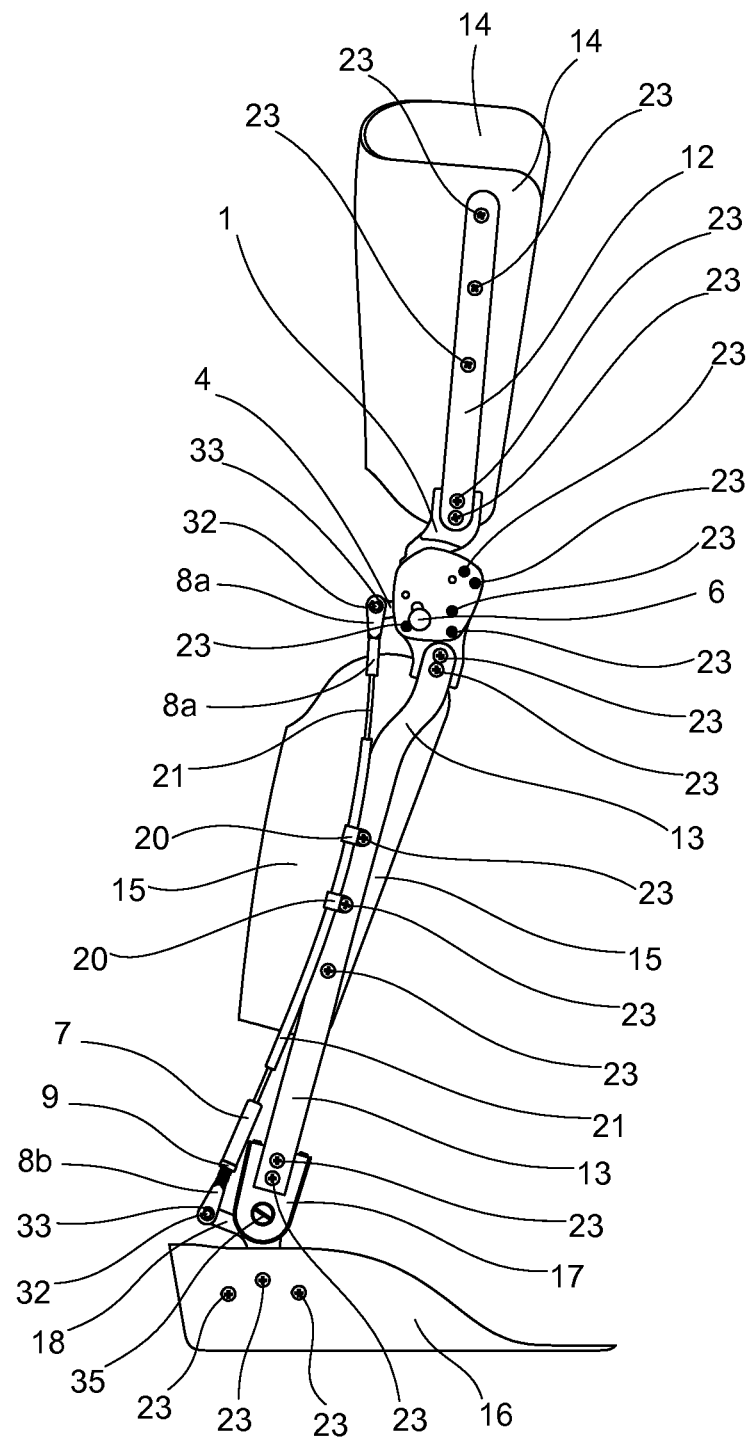
FIG. 6 is a right side view of a knee-ankle-foot orthotic device incorporating the knee joint assembly of the present invention shown with the ankle dorsiflexed and the knee joint beginning to unlock.
Figure 12:
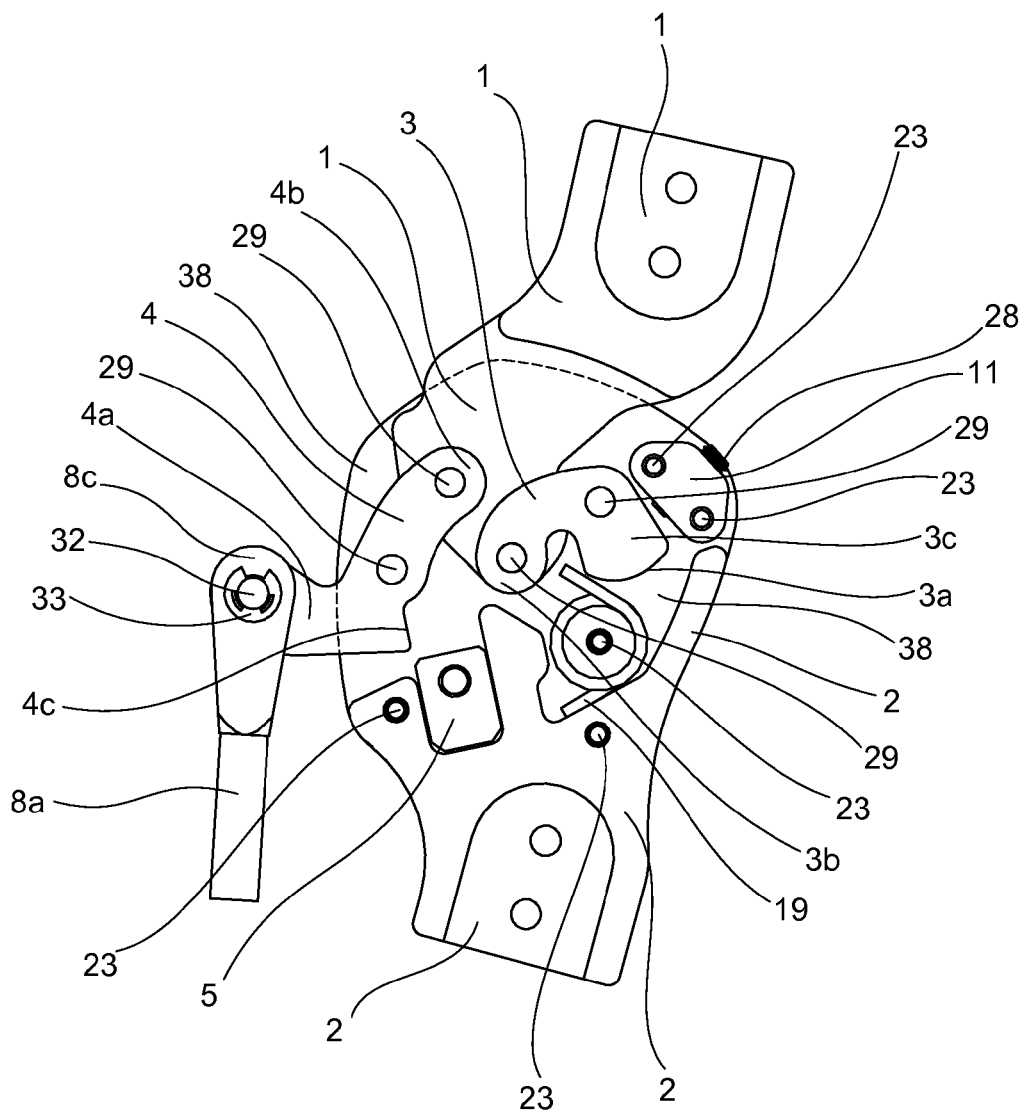
FIG. 12 is a detail view of the knee joint assembly of the present invention corresponding to the view shown in FIG. 6.
Figure 13:
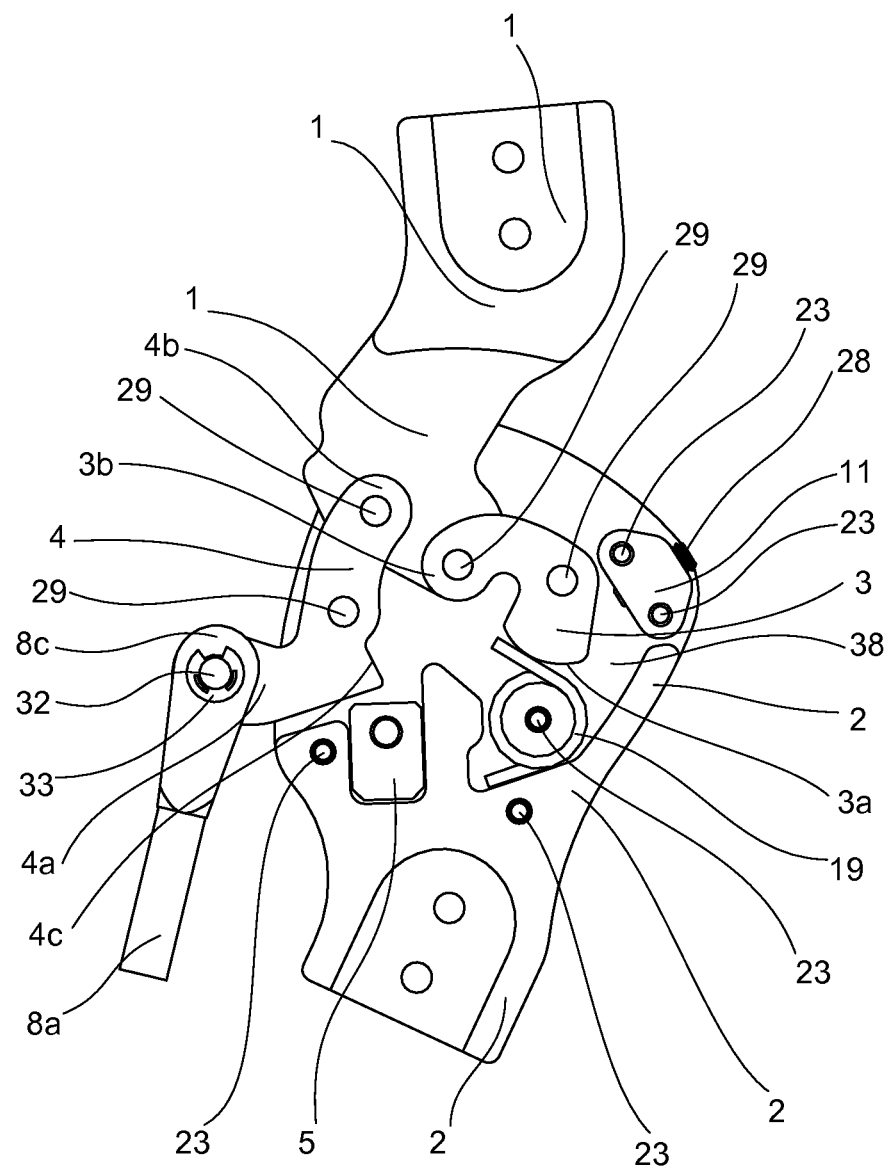
FIG. 13 is a detail view of the knee joint assembly of the present invention corresponding to the view shown in FIG. 7.

FIG. 12 is a detail view of the knee joint assembly of the present invention corresponding to the view shown in FIG. 6 (just prior to the knee joint unlocking), and FIG. 13 is a detail view of the knee joint assembly corresponding to the view shown in FIG. 7 (just after the knee joint has unlocked). The point at which the knee joint unlocks is when the second end portion 3c of the first link 3 rotates approximately fifteen degrees (15°) downward. As this link rotates downward, the second end of the coil spring 19 exits the recess in the first link and makes contact with the first arcuate edge 3a of the first link 3. When the first link 3 rotates upward, the second end of the coil spring 19 snaps back into this recess and the coil spring 19 acts to push the knee joint back into full extension. When the second end portion 3c of the first link 3 abuts up against the extension stop 11, the knee joint is locked again.

In FIGS. 12 and 13, the cable 21 (not shown) that is attached to the cable clevis 8a has been pulled downward by virtue of the dorsiflexion of the ankle. When the cable clevis 8a is pulled downward, the first end portion 4a of the second link 4 rotates downward, and the second end portion 4b of the second link 4 rotates outward. At the same time, because of the pin 29 connecting the second end portion 4b of the second link 4 to the upper plate 1, the upper plate also moves in an outward direction (in this case, "outward" means in the direction of the knee flexing). As the upper plate 1 moves in an outward direction, because of the pin 29 connecting the first end portion 3b of the first link 3 to the upper plate 1 and the pin 29 connecting the second end portion 3c of the first link 3 to the back plate 38, the first end portion 3b of the first link 3 rotates upward, and the second end portion 3c of the first link 3 rotates downward.

Figure 15:
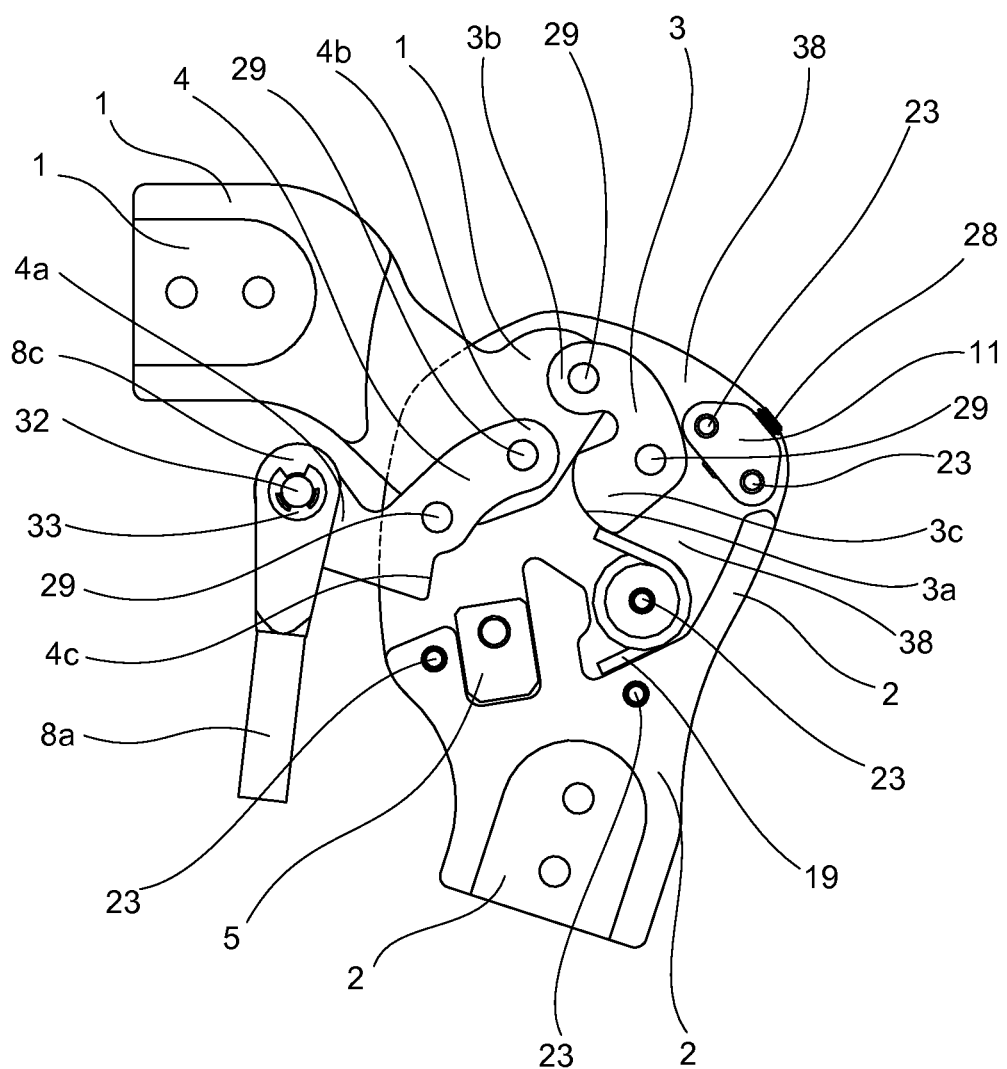
FIG. 15 is a detail view of the knee joint assembly of the present invention with the knee joint in a fully flexed position.

To go from the position shown in FIG. 13 to the fully flexed knee position shown in FIG. 15, the first end portion 4a of the second link 4 rotates upward, the second end portion 4b of the second link 4 rotates inward, the first end portion 3b of the first link rotates further upward, and the second end portion 3c of the first link 3 rotates inward.

Figure 14:
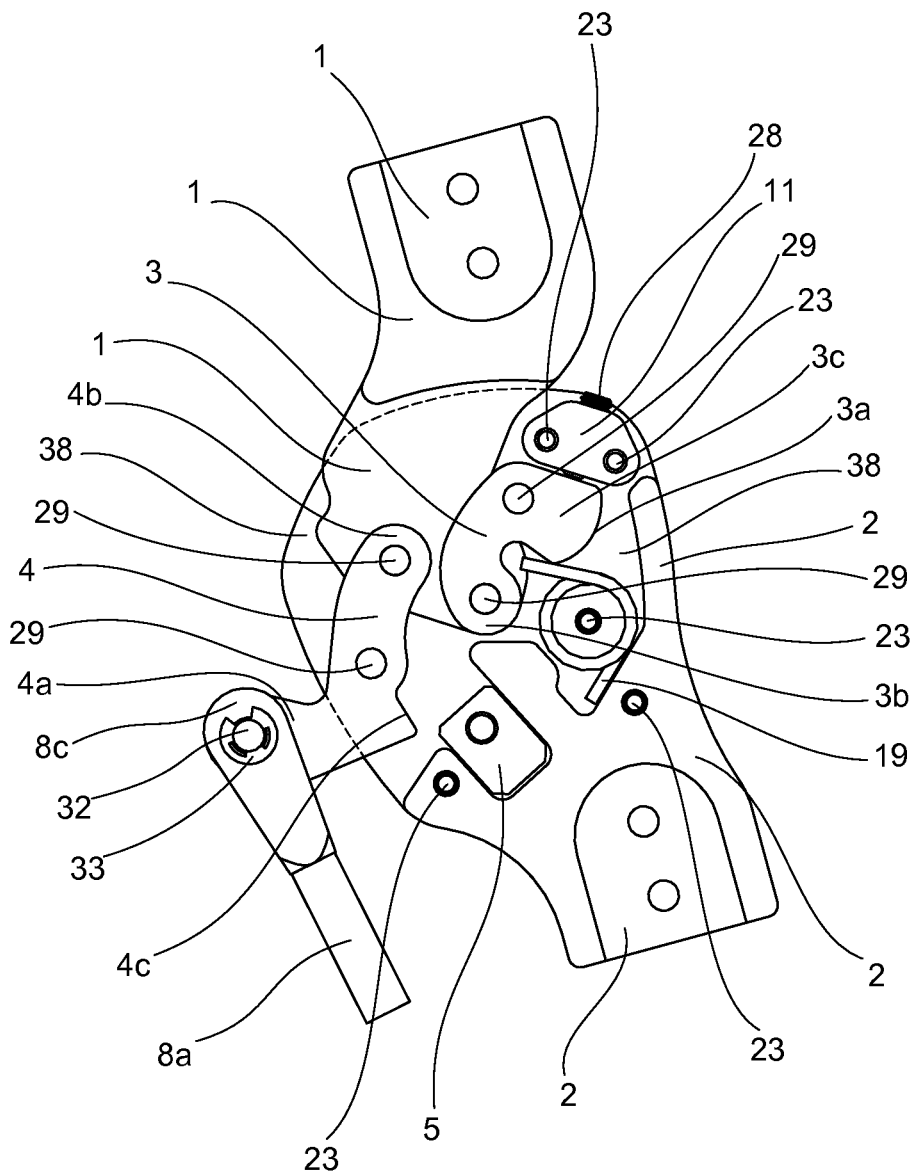
FIG. 14 is a detail view of the knee joint assembly of the present invention corresponding to the view shown in FIG. 8.

FIG. 14 is a detail view of the knee joint assembly of the present invention corresponding to the view shown in FIG. 8. This is the same view as that shown in FIG. 10 except that the leg is at a different angle.

Figure 16A:
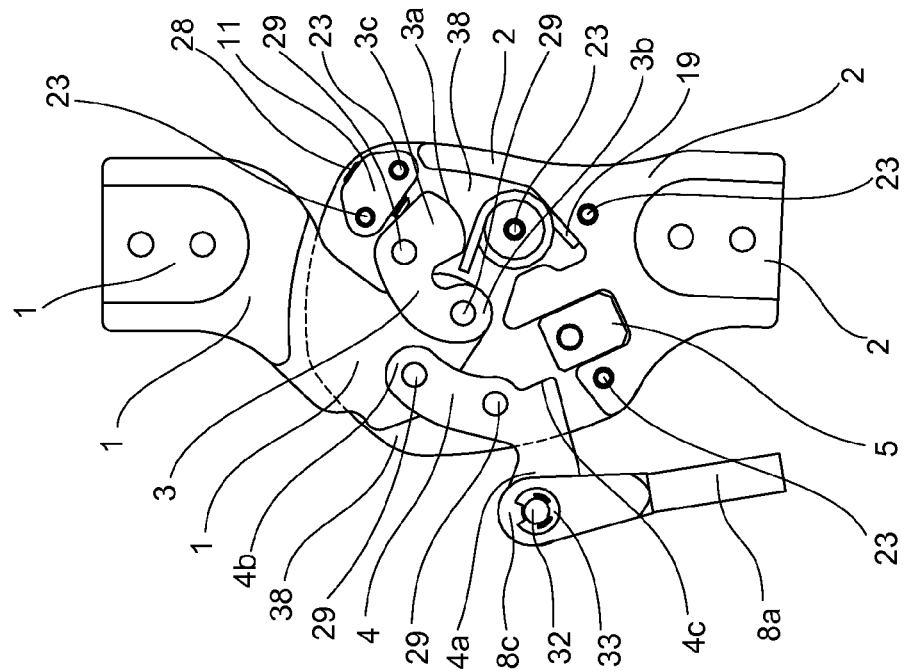
FIG. 16A is a detail view of the knee joint assembly with the set screw in the outermost position.
Figure 16B:
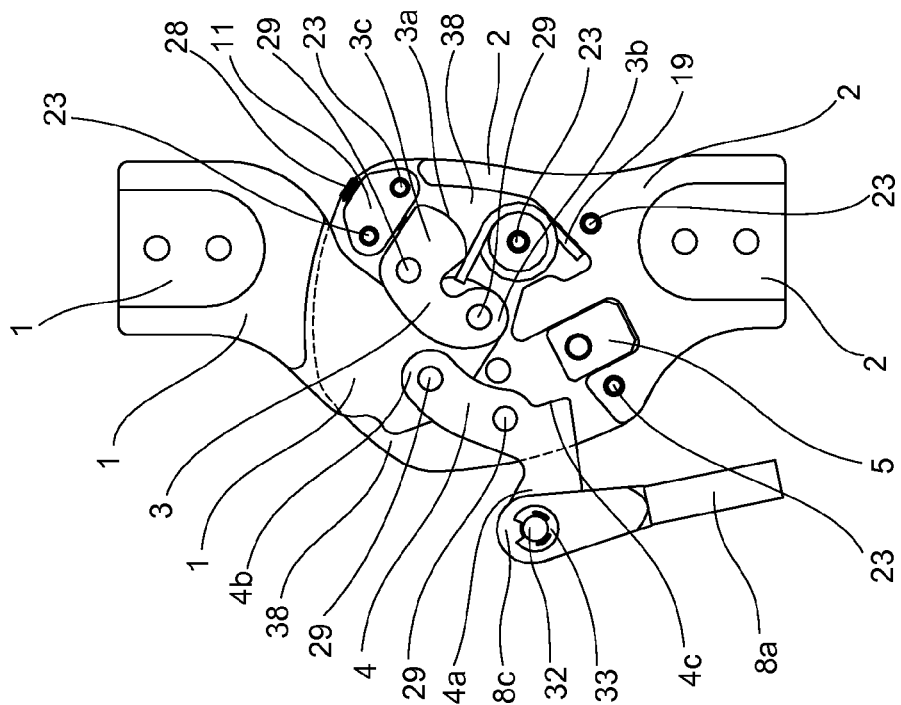
FIG. 16B is a detail view of the knee joint assembly with the set screw turned down to adjust the resting position of the knee.

FIGS. 16A and 16B illustrate the adjustability of the extension stop 11. As shown in these figures, the extension stop screw 28 extends through the extension stop 11 and comes into contact with the first link 3 (more specifically, the second end portion 3c of the first link 3), thereby limiting the degree of rotation of the first link 3. When the extension stop screw 28 is screwed down fully, as shown in FIG. 16B, it prevents the knee joint from fully extending and locking. This configuration would be preferable if the caregiver wanted to allow the patient free motion (in other words, the mechanical joint does not lock). The extension stop screw 28 can also be tightened slightly so that it causes the knee joint to unlock more quickly while allowing full extension and locking of the knee joint. This adjustment, in combination with the cable length adjustment described below, allows the provider to fine-tune the sensitivity of the joint unlock mechanism.

FIGS. 17A and 17B illustrate the functionality of the lock 5. As in FIG. 11-14, the knob 6 has been omitted for clarity. Note that the lock 5 is situated within a channel within the lower plate 2. When the lock 5 is in a downward position, as shown in FIGS. 11-14, the knee joint is allowed to flex and extend, as described above; however, when the lock 5 is moved manually into an upward position, as shown in FIGS. 17A and 17B, the knee is only allowed to flex approximately three degrees (3°). Within this range of flexion, the coil spring 19 acts to push the knee joint back into full extension, thereby providing some shock absorption to the person using the joint. The degree of flexion is limited by the inner wall 4c of the second link 4 coming into contact with the side wall of the lock 5 (see FIG. 17B). Note that the lock 5 can only be moved into an upward position when the knee joint is within approximately three degrees (3°) of full extension; therefore, the knee joint cannot be locked in a flexed position greater than approximately three degrees (3°).

FIG. 18A is a detail view of the ankle assembly with the cable adjustment barrel tightened, and FIG. 18B is a detail view of the ankle mechanism with the cable adjustment barrel loosened. As these figures illustrate, the overall length of the cable 21 may be adjusted by tightening or loosening the cable adjustment barrel 7 on the cable clevis 8b, which is threaded. As noted above, a shorter cable will cause the knee joint to unlock more quickly than a longer cable.

Figure 19:
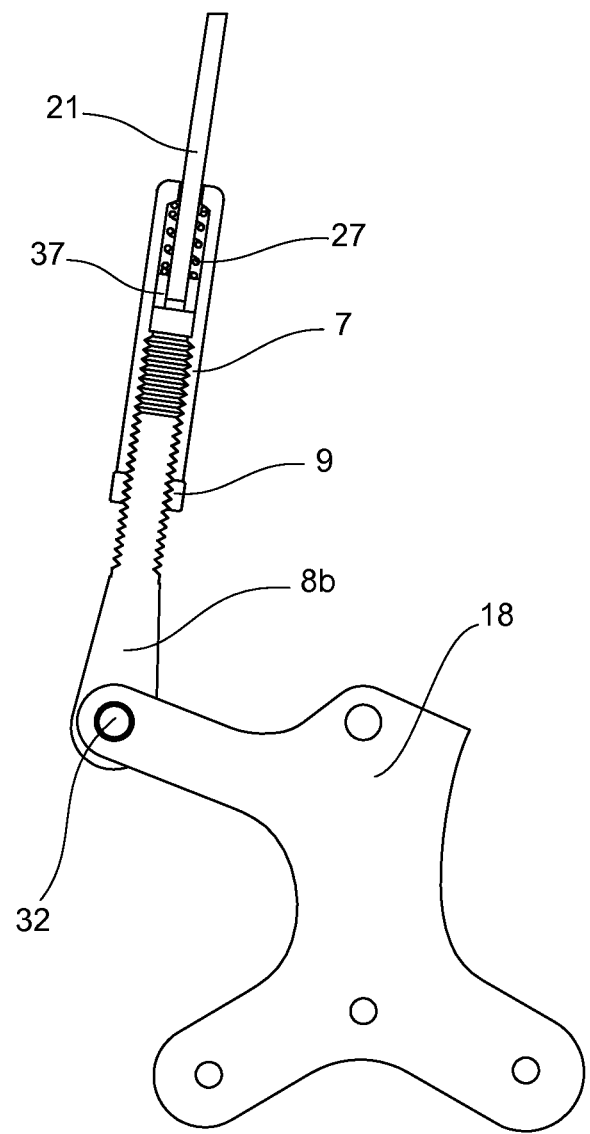
FIG. 19 is a cross-section view of the cable tension adjustment mechanism.

FIG. 19 is a cross-section view of the cable tension adjustment mechanism. This figure shows that the cable adjustment barrel 7 threads down onto the cable clevis 8b. It also shows the strain relief spring 27 that is located inside of the cable adjustment barrel 7. The purpose of the strain relief spring 27 is to prevent undue strain from being placed on the cable.

Figure 20:
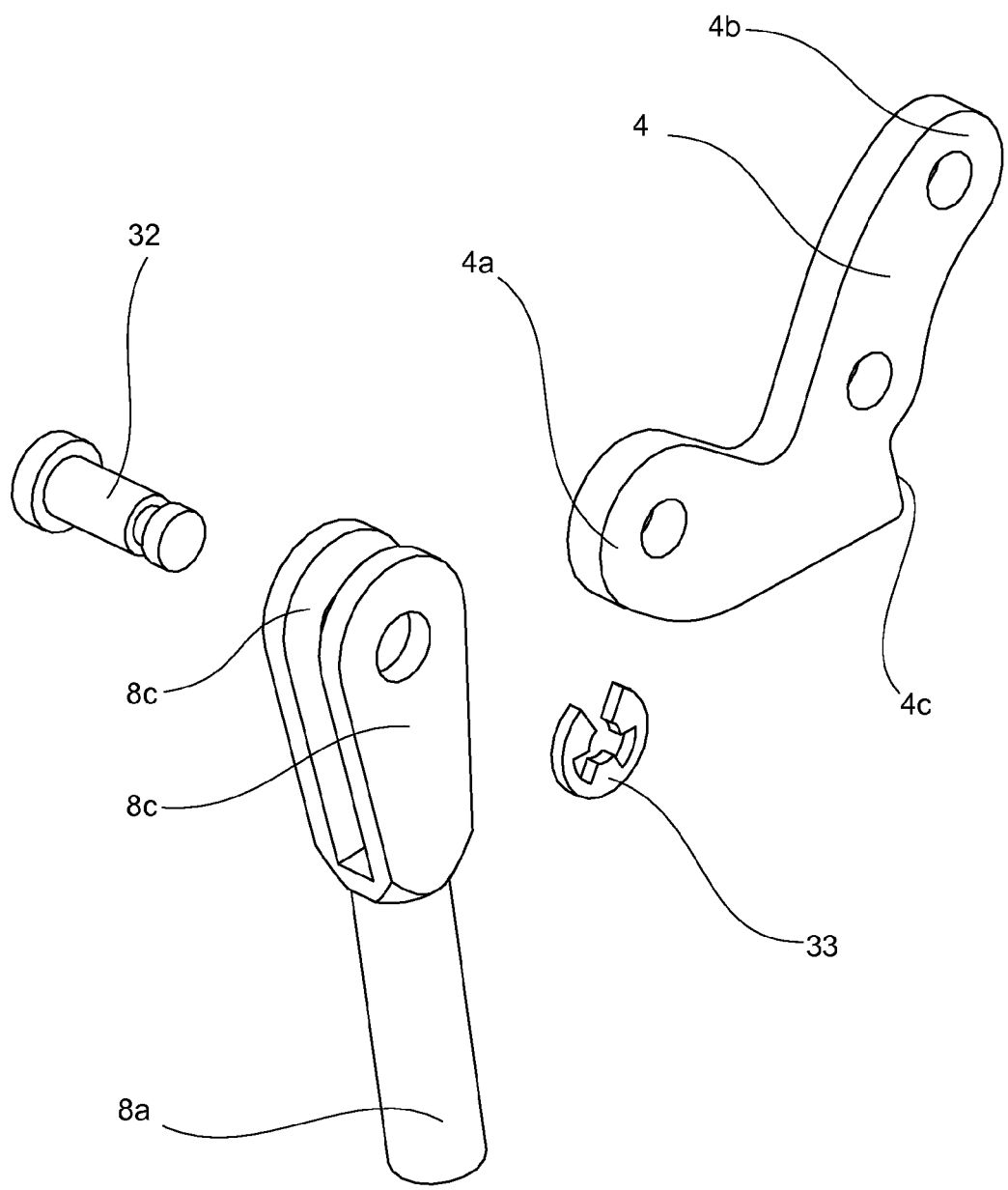
FIG. 20 is an exploded detail view of the cable clevis attachment.

FIG. 20 is an exploded detail view of the cable clevis attachment. As shown in this figure, a cable pin 32 extends through the top part of the cable clevis 8a and is held in place with a retaining clip 33. The cable pin 32 also extends through the first end portion 4a of the second link 4, which is inserted in between twin brackets 8c of the cable clevis 8a. In this manner, the cable clevis 8a is pivotally attached to the first end portion 4a of the second link 4. Although only the non-threaded cable clevis 8a is shown, the same attachment mechanism is used with the threaded cable clevis 8b.

Note that although the cable adjustment barrel 7 is shown in FIGS. 18A-20 as being on the bottom end of the cable 21, it could also be situated on the top end of the cable 21, where cable clevis 8a is shown. The invention is not restricted to the cable adjustment barrel 7 being on any particular end of the cable 21.

Figure 21:
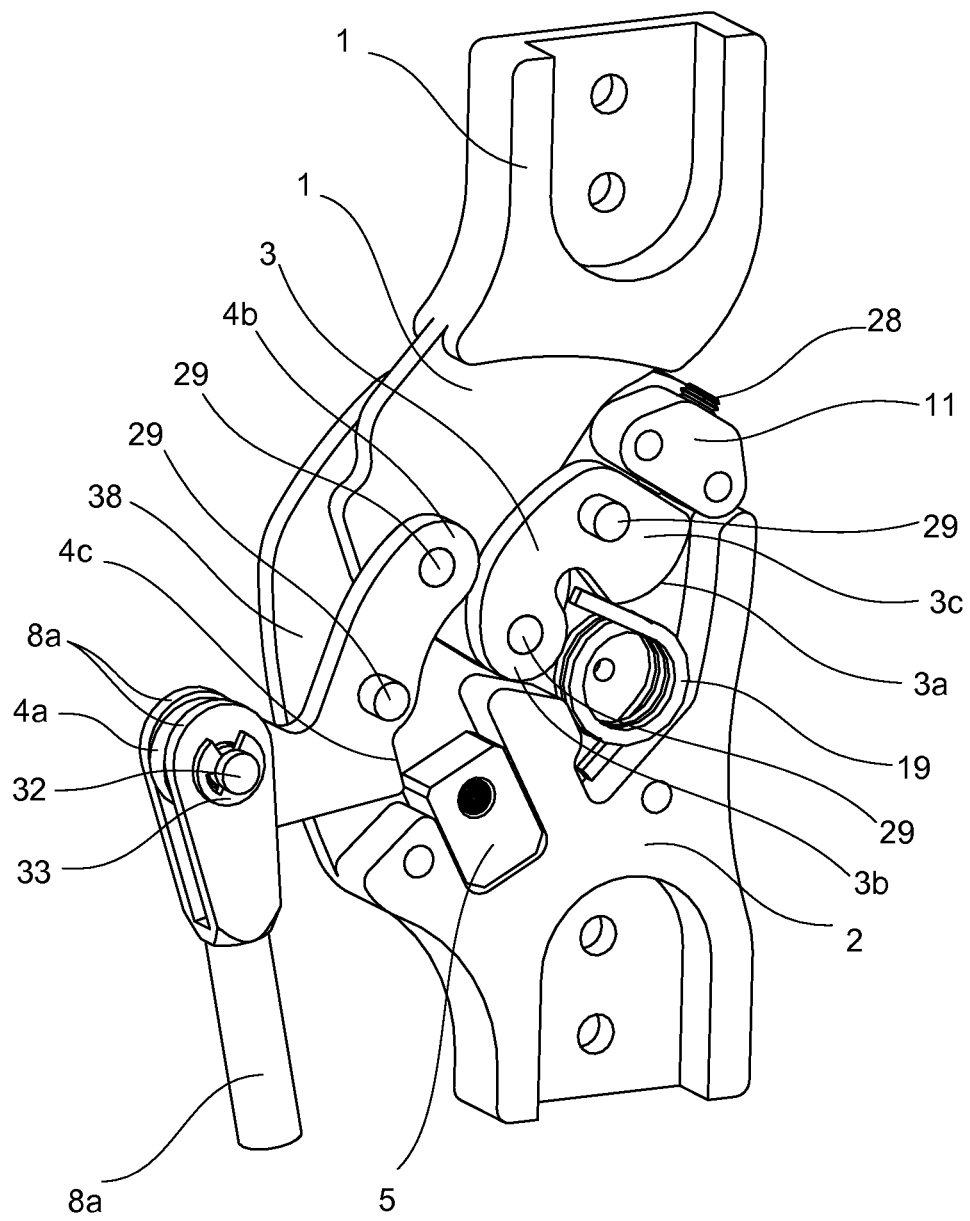
FIG. 21 is a perspective view of the knee joint assembly with the cover plate removed.

FIG. 21 is a perspective view of the knee joint assembly with the cover plate removed. This figure shows the threaded hole in the lock 5 into which the knob 6 (not shown) is inserted. In this figure, the knee joint is in a fully extended and automatically locked position. The term "automatically locked" refers to the fact that the knee joint cannot flex until and unless the cable 21 (not shown) is pulled downward by virtue of the ankle dorsiflexing. In this figure, the manual lock 5 has not been engaged and is, therefore, in an unlocked position. With the manual lock 5 in an engaged (upward) position, the knee joint will not flex beyond approximately three degrees (3°) even when the ankle is dorsiflexed and the cable 21 (not shown) pulled downward.

Figure 22:
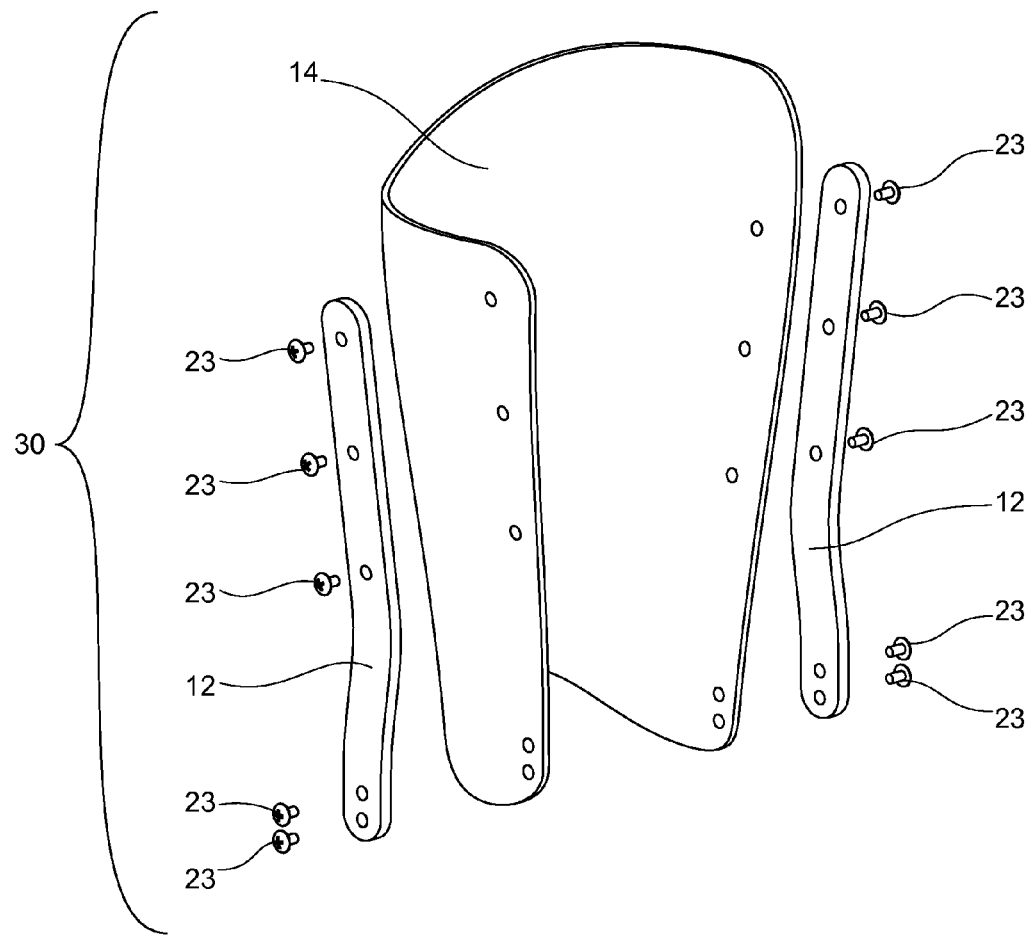
FIG. 22 is an exploded view of the upper leg assembly of the present invention.
Figure 23:
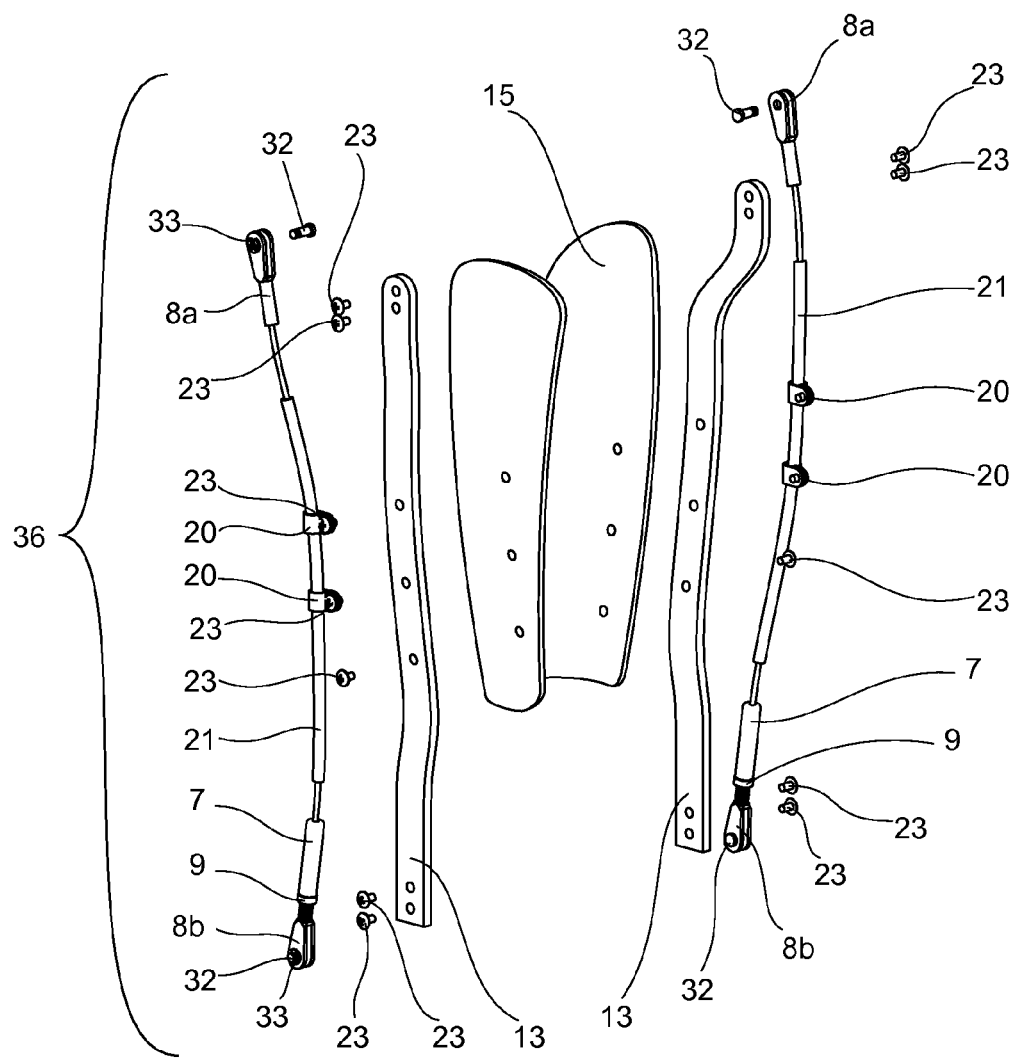
FIG. 23 is an exploded view of the lower leg assembly of the present invention.

FIG. 22 is an exploded view of the upper leg assembly of the present invention, and FIG. 23 is an exploded view of the lower leg assembly of the present invention. All parts shown in these two figures have been previously described.

Figure 24:
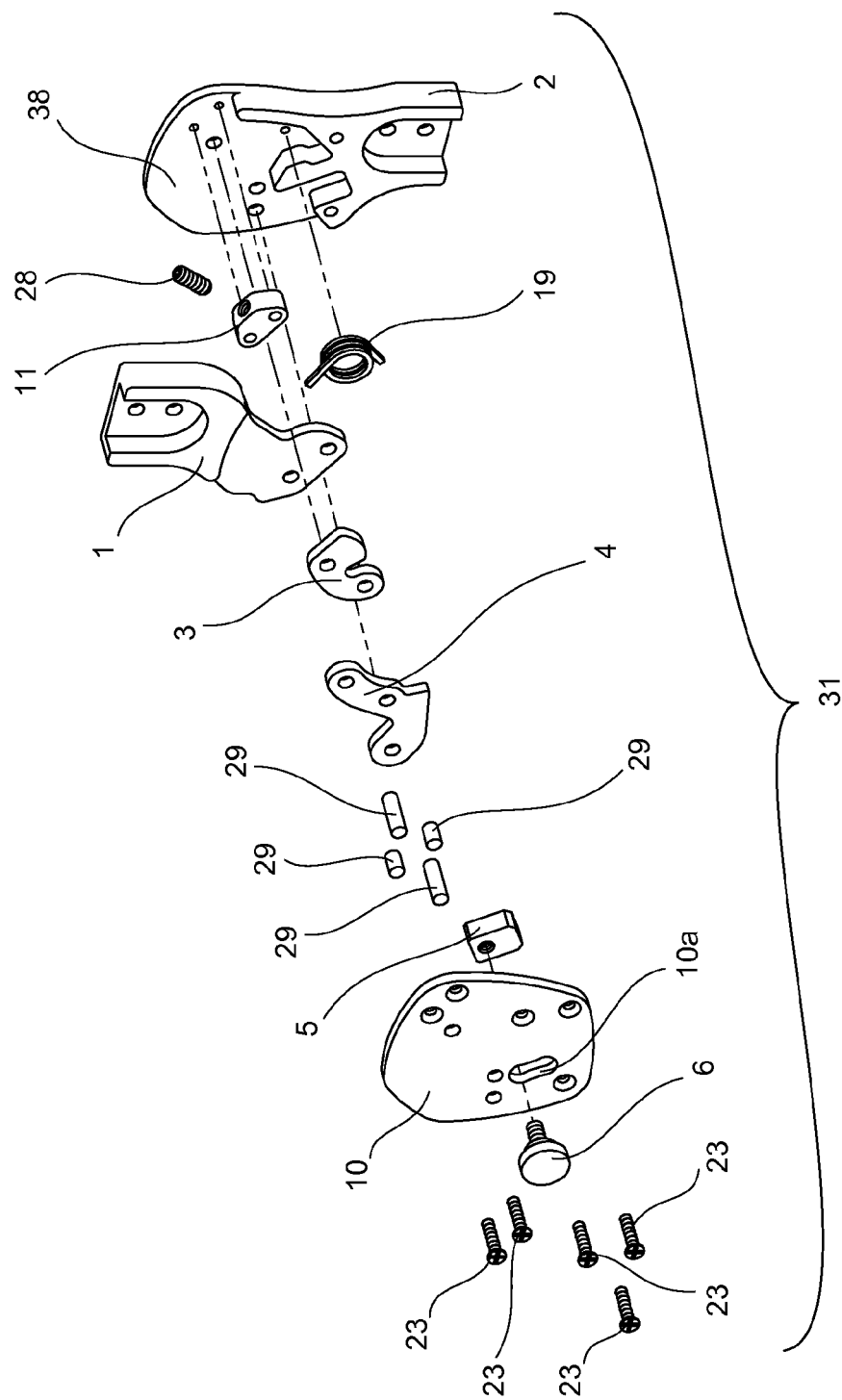
FIG. 24 is an exploded view of the knee joint assembly of the present invention.

FIG. 24 is an exploded view of the knee joint assembly of the present invention. This figure shows the aperture 10*a* through which the threaded portion of the knob 6 extends. The threaded portion of the knob 6 also extends into the lock 5. Note that the aperture 10*a* is shaped so as to allow for a "downward" position and an "upward" position of the lock 5.

Figure 25:
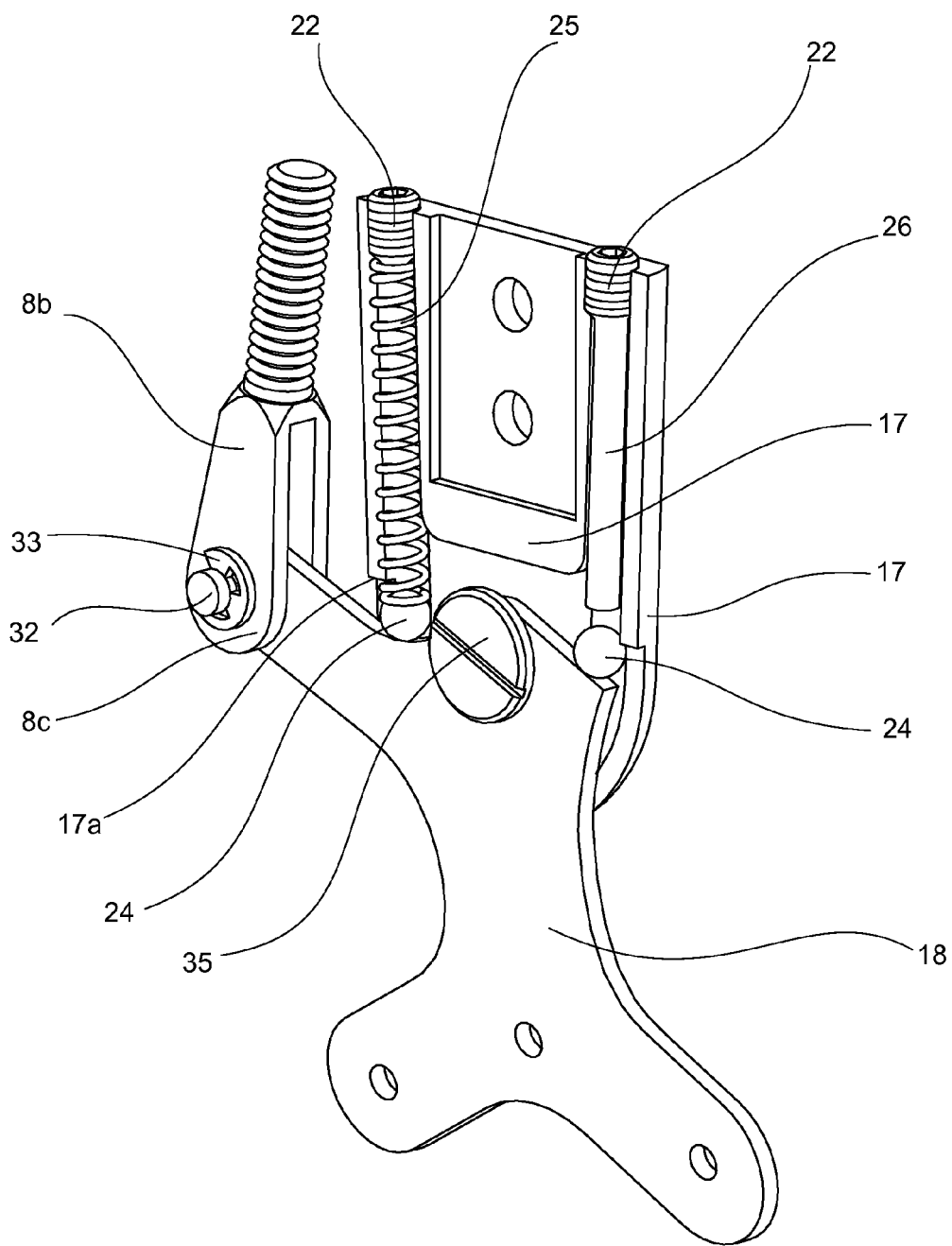
FIG. 25 is a cutaway view of the ankle assembly.

FIG. 25 is a cutaway view of the ankle assembly. As shown in this figure, inside and in the rear end of the ankle bracket 17 are a set screw 22, an ankle spring 25, and a ball bearing 24. The set screw 22 screws adjusts the tension on the ankle spring 25. When the ankle is plantarflexed, the extent of plantarflexion is limited by one of two things—either the full compression of the ankle spring 25 (i.e., the spring cannot compress any further) or the bottom edge 17*a* or the ankle bracket 17 coming into contact with the stirrup 18. By tightening the spring down, the extent of plantarflexion is decreased; conversely, by loosening the spring, the extent of plantarflexion is increased (at least until the edge 17*a* of the ankle bracket 17 comes into contact with the stirrup 18).

Inside and in the front end of the ankle bracket 17 are a set screw 22, a rod 26, and a ball bearing 24. When the ankle is not dorsiflexed, the rod 26 extends longitudinally down one side of the ankle bracket 17 and ends short of the stirrup 18. In the space between the stirrup 18 and the end of the bar 26 is a ball bearing 24. The ankle can be dorsiflexed until the rod 26 comes into contact with the ball bearing 24, at which point the rod 26 provides a hard stop to prevent further dorsiflexion. The set screw 22 adjusts the position of the rod 26 relative to the ball bearing (i.e., increases or decreases the space between the rod 26 and ball bearing 24) so that a caregiver can increase or decrease the degree of dorsiflexion allowed.

Note that the set screw 22, ankle spring 25 and ball bearing 24 on the rear end of the ankle bracket 17 and the set screw 22, rod 26 and ball bearing 24 on the front end of the ankle bracket 17 are situated within channels in the interior of the ankle bracket 17. In a preferred embodiment, the ankle is allowed to flex approximately ten degrees (10°).

Although the preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. An orthotic joint comprising:
   (a) an upper plate;
   (b) a lower plate;
   (c) a cover plate;
   (d) back plate;
   (e) a first link;
   (f) a second link;
   (g) a coil spring that is situated between the lower plate and first link, wherein the coil spring comprises a first end, and wherein as the joint is flexed, the first end of the coil spring travels along a first arcuate edge of the first link; and
   (h) an extension stop that is situated adjacent to the first link;
   wherein a first pin pivotally connects the first link to the upper plate, and a second pin pivotally connects the first link to the back plate;
   wherein a third pin pivotally connects the second link to the upper plate, and a fourth pin pivotally connects the second link to the back plate; and
   wherein the upper plate is attached to an upper leg brace, the lower plate is attached to a lower leg brace, the upper leg brace is attached to at thigh support, and the lower brace as attached to a calf support;
   further comprising a cable with a first end and a second end, wherein the cable is secured to the upper and lower leg braces, and wherein the first end of the cable is attached to a first cable clevis, and the second end of the cable is attached to a second cable clevis;
   wherein the second link comprises a first end portion and a second end portion, and wherein the first cable clevis is pivotally attached to the second link such that when the cable is pulled downward, the first end portion of the second link rotates downward, and the second end portion of the second link rotates outward;
   wherein when the second end portion of the second link rotates outward, the upper plate moves in an outward direction;
   wherein the first link comprises a lint end portion and a second end portion, and when the upper plate moves in an outward direction, the first end portion of the first link rotates upward, and the second end portion of the first link rotates downward;
   wherein the second cable clevis is pivotally attached to a stirrup; and
   wherein the stirrup is attached to a foot support and an ankle bracket.

2. The knee-ankle-foot orthotic device of claim 1, wherein the second cable clevis is threadably connected to a cable adjustment barrel, wherein the cable has a length, and wherein the length of the cable is adjusted by tightening and loosening the cable adjustment barrel on the second cable clevis.

3. The knee-ankle-foot orthotic device of claim 1, wherein the first cable clevis is threadably connected to a cable adjustment barrel, wherein the cable has a length, and wherein the length of the cable is adjusted by tightening and loosening the cable adjustment barrel on the first cable clevis.

4. The knee-ankle-foot orthotic device of claim 2 or 3, further comprising a strain relief spring that is located inside of the cable adjustment barrel.

5. The knee-ankle-foot orthotic device of claim 1, wherein when the joint goes from an unlocked and partially flexed position to a fully flexed position, the first end portion of the second link rotates upward, the second end portion of the second link rotates inward, the first end portion of the first link rotates upward, and the second end portion of the first link rotates inward.

6. The knee-ankle-foot orthotic device of claim 1, wherein the ankle bracket comprises a first internal channel and as second internal channel;
   wherein within the first internal channel are an ankle spring, a ball bearing situated on a first end of the ankle spring, and a set screw situated on a second end of the ankle spring, wherein the set screw adjusts compression of the ankle spring; and
   wherein within the second internal channel are a rod, a ball bearing situated adjacent to a first end of the rod, and a set screw situated on as second end of the rod, wherein the set screw adjusts the position of the first end of the rod relative to the ball bearing.

7. The knee-ankle-foot orthotic device of claim 6, wherein the first internal channel is located in a rear end of the ankle bracket, and the second internal channel is located in a front end of the ankle bracket.

8. An orthotic joint comprising:
   (a) an upper plate;
   (b) a lower plate;
   (c) a cover plate;
   (d) back plate;
   (e) a first link;
   (f) a second link;
   (g) a coil spring that is situated between the lower plate and first link, wherein the coil spring comprises a first end, and wherein as the joint is flexed, the first end of the coil spring travels along a first arcuate edge of the first link; and
   (h) an extension stop that is situated adjacent to the first link;
   wherein a first pin pivotally connects the first link to the upper plate, and a second pin pivotally connects the first link to the back plate; and
   wherein a third pin pivotally connects the second link to the upper plate, and a fourth pin pivotally connects the second link to the back plate,
   further comprising a lock and a knob, wherein the knob is attached to the lock and allows the position of the lock relative to the second link to be adjusted, wherein the second link comprises an inner wall, and wherein when the lock is in a locked position, the inner wall of the second link is in contact with the lock.

9. The orthotic joint of claim 8, wherein the lock is situated within a channel in the lower plate.

10. An orthotic joint comprising:
   (a) an upper plate;
   (b) a lower plate;
   (c) a cover plate;
   (d) back plate;
   (e) a first link;
   (f) a second link;
   (g) a coil spring that is situated between the lower plate and first link, wherein the coil spring comprises a first end, and wherein as the joint is flexed, the first end of the coil spring travels along a first arcuate edge of the first link; and
   (h) an extension stop that is situated adjacent to the first link;
   wherein a first pin pivotally connects the first link to the upper plate, and a second pin pivotally connects the first link to the back plate; and
   wherein a third pin pivotally connects the second link to the upper plate, and a fourth pin pivotally connects the second link to the back plate,
   further comprising an extension stop screw that is threadably inserted through the extension stop, wherein the extension stop screw adjusts the position of the second end portion of the first link relative to the extension stop.

* * * * *